(12) United States Patent
Xi et al.

(10) Patent No.: US 10,899,787 B2
(45) Date of Patent: Jan. 26, 2021

(54) CYTARABINE PRODRUG NUCLEOSIDE CYCLIC PHOSPHATE COMPOUND BASED ON LIVERSPECIFIC DELIVERY AND USE

(71) Applicant: ZHEJIANG PALO ALTO PHARMACEUTICALS, INC., Quzhou (CN)

(72) Inventors: Zhijian Xi, Quzhou (CN); Huaqiang Xu, Quzhou (CN); Chunping Lu, Quzhou (CN); Zhongshan Wu, Quzhou (CN)

( * ) Notice: Subject to any disclaimer, the term of this patent is extended or adjusted under 35 U.S.C. 154(b) by 0 days.

(21) Appl. No.: 16/907,215

(22) Filed: Jun. 20, 2020

(65) Prior Publication Data

US 2020/0317711 A1    Oct. 8, 2020

Related U.S. Application Data

(63) Continuation of application No. PCT/CN2018/122822, filed on Dec. 21, 2018.

(30) Foreign Application Priority Data

Dec. 22, 2017    (CN) .......................... 2017 1 1408942

(51) Int. Cl.
*C07H 19/10*    (2006.01)
*C07H 19/11*    (2006.01)

(52) U.S. Cl.
CPC ............. *C07H 19/10* (2013.01); *C07H 19/11* (2013.01)

(58) Field of Classification Search
None
See application file for complete search history.

(56) References Cited

U.S. PATENT DOCUMENTS

| | | |
|---|---|---|
| 7,148,349 B2 | 12/2006 | Reddy et al. |
| 2009/0118223 A1 | 5/2009 | Erion et al. |
| 2019/0233463 A1 | 8/2019 | Bogen et al. |

FOREIGN PATENT DOCUMENTS

| | | |
|---|---|---|
| CN | 102164939 A | 8/2011 |
| CN | 103393709 A | 11/2013 |

OTHER PUBLICATIONS

Boyer et al., Journal of Medicinal Chemistry, 2006, vol. 49, 7711-7720. (Year: 2006).*
Internation Search Report of PCT/CN2018/122822, dated Mar. 22, 2019.
Boyer, S.H. et al., "Synthesis and Characterization of a Novel Liver-Targeted Prodrug of Cytosine-1-β-D-arabinofuranoside Monophosphate for the Treatment of Hepatocellular Carcinoma", J.Med.Chem.,vol. 49, No. (16), Dec. 12, 2006 (Dec. 21, 2006) pp. 7711-7720.

(Continued)

*Primary Examiner* — Traviss C McIntosh, III
(74) *Attorney, Agent, or Firm* — W&K IP

(57) ABSTRACT

Disclosed are an anticancer prodrug nucleoside cyclic phosphate compound based on liver-specific delivery (LSD) technology and the use thereof, in particular, provided are a compound of formula (I) and an isomer, a pharmaceutically acceptable salt, a hydrate, a solvate and a corresponding pharmaceutical composition thereof, and the use of the compound alone or in combination with other anticancer drugs against cancer, especially in treating hepatic carcinoma (HCC).

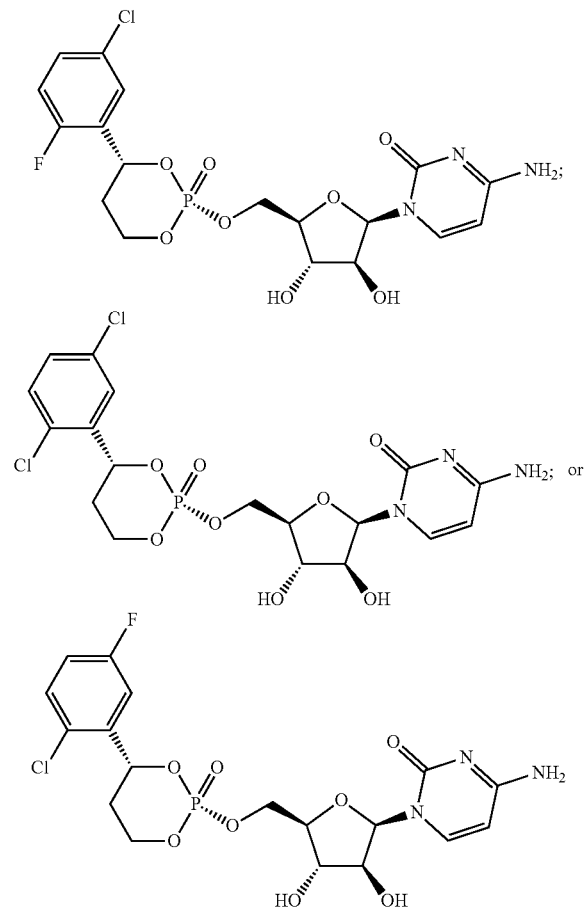

4 Claims, No Drawings

(56) References Cited

OTHER PUBLICATIONS

Erion, M. D. et al. "Design, Synthesis, and Characterization of a Series of Cytochrome P450 3A-Activated Prodrugs (HepDirect Prodrugs) Useful for Targeting Phosph(on)ate-Based Drugs to the Liver", J.Am.Chem.Soc., vol. 126, No. (16), Apr. 2, 2004 (Apr. 2, 2004), pp. 5154-5163.

Carroll, S.S. et al. "Antiviral Efficacy upon Administration of a HepDirect Prodrug of 2'-C-Methylcytidine to Hepatitis C Virus-Infected Chimpanzees", Antimicrobial Agents and Chemotherapy, vol. 55, No. (8), May 31, 2011 (May 31, 2011), pp. 3854-3860.

\* cited by examiner

CYTARABINE PRODRUG NUCLEOSIDE CYCLIC PHOSPHATE COMPOUND BASED ON LIVERSPECIFIC DELIVERY AND USE

CROSS-REFERENCE TO RELATED APPLICATIONS

The present disclosure is a continuation application of International Application No. PCT/CN2018/122822 filed Dec. 21, 2018, and claims priority to Chinese Application No. 201711408942.3 filed on Dec. 22, 2017, which are incorporated herein by reference.

TECHNICAL FIELD

The present disclosure relates to the preparation and use of a liver specific delivery (LSD)-based anticancer prodrug nucleoside cyclic phosphate compound, or an optical isomer, a hydrate, a solvate, a pharmaceutically acceptable salt and a pharmaceutical composition thereof.

BACKGROUND ART

Liver cancer, is a primary malignant tumor occurring in the liver, and commonly occurs in patients suffering from liver cirrhosis or liver fibrosis. As reported by WHO, there are more than 700 thousands of cases dying from liver cancer every year worldwide, and the liver cancer is the second deadly cancer. Viral hepatitis is an important cause of liver cancer, and Asia and Africa are regions with the highest incidence of liver cancer due to prevalence of viral hepatitis type b and c. At present, treatment for liver cancer is a multidisciplinary comprehensive treatment, and mainly includes operations, local ablation treatment, interventional therapy, radiotherapy, chemotherapy, targeted therapy and so on.

At, present, nucleoside chemotherapeutic drugs for treatment of liver cancer are limited, only fluorouracil is used for second-line treatment, and cytarabine is, not suitable for solid tumors such as liver cancer. Cytarabine needs to be converted into a monophosphate form through the action of deoxycytidine kinase in cells, and then is further phosphorylated into a triphosphate form, so that the DNA replication of tumor cells can be inhibited, and due to the lack of deoxycytidine kinase in solid tumors, active ingredients in the solid tumors are few, and the treatment effect is poor.

Utilizing liver specific delivery technology, the present disclosure bypasses the phosphorylation step of deoxycytidine kinase, and successfully improves the concentration of active ingredients in the liver.

The cyclic phosphate modified cytarabine prodrug is metabolized by CYP3A enzyme in the liver, and does not need deoxycytidine kinase to generate monophosphate compound. Specifically, the precursor structure of cyclic phosphate (4-aryl-2-oxo-1,3,2-dioxaphosphorinane) has very good liver specific delivery performance, and the mechanism is very clear, i.e., 4-aryl substitution position is specifically catalyzed by CYP3A in, cytochrome P450 isoenzyme family in hepatocytes to generate hydroxyl, then ring-opening is carried out to generate phosphate intermediate with negative charge, which substance is not easy to penetrate through the cell membrane, and thus exists in the cell, and under the catalysis of phosphodiesterase, nucleotide monophosphate compound is generated through hydrolysis and β-elimination reaction. Nucleotide triphosphate compound with biological activity is generated continuously under, the action of nucleotide kinase, and meanwhile, metabolic byproduct aryl vinyl ketone can be eliminated through 1,4-addition reaction with glutathione which is rich in hepatocytes and can resist oxidation and free radicals, and no report has been made that this addition product has side effects.

Cytarabine has relatively large toxic and side effects, and the liver specific delivery technology is utilized to enhance the concentration in the liver, which is beneficial to reducing the toxic and, side effects.

At present, there is no anti-liver-tumor drug with high activity, strong liver delivery property and low side effects. Therefore, there is an urgent need in the art to develop a highly active anti-tumor drug, having stronger liver specificity and low side effects.

SUMMARY

The present disclosure synthesizes anti-cancer cytarabine cyclic phosphate, and then further modifies an aromatic ring substituent thereof to obtain a class of prodrugs with better liver delivery effect, so that the present disclosure has the advantages of higher curative effect and less toxic and side effect.

A first aspect of the present disclosure provides a compound represented by formula I, or an optical isomer, a pharmaceutically acceptable salt, a hydrate or a solvate thereof:

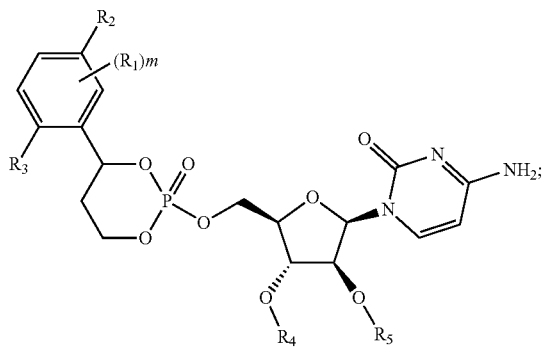

wherein each R1 is independently selected from the group consisting of halogen, nitro, hydroxyl, amino, cyano, substituted or unsubstituted C1-C6 alkyl, substituted or unsubstituted C3-C8 cycloalkyl, substituted or unsubstituted C1-C6 alkoxy, substituted or unsubstituted C1-C6 alkylamino, —COOH, substituted or unsubstituted C2-C6 alkylcarboxyl, substituted or unsubstituted C2-C6 ester group, substituted or unsubstituted C2-C6 alkanoyl, and substituted or unsubstituted C2-C6 alkylamido, wherein the "substituted" means having one or more substituents selected from the group consisting of halogen, C1-C3 alkyl, C1-C3 haloalkyl, nitro, hydroxy, amino, and cyano;

R2 and R3 are each independently halogen (F or Cl);

R4 and R5 are each independently selected from the group consisting of: hydrogen, substituted or unsubstituted C1-C10 alkyl, substituted or unsubstituted C3-C10 cycloalkyl, substituted or unsubstituted C2-C12 alkanoyl, and substituted or unsubstituted C2-C11 ester group (i.e., —CO—O—C1-C10 alkyl), wherein the "substituted" means having one or more substituents selected from the group consisting of: halogen, C1-C3 alkyl, C1-C3 haloalkyl, nitro, hydroxy, —NRaRb, and cyano, and wherein Ra and Rb are each independently H, C1-C3 alkyl, C3-C6 cycloalkyl, or C1-C3 haloalkyl; and m is 0, 1, 2 or 3.

In an embodiment, R4 and R5 are each independently selected from the group consisting of hydrogen, substituted or unsubstituted C1-C6 alkyl, substituted or unsubstituted C3-C8 cycloalkyl, substituted or unsubstituted C2-C6 ester group, and substituted or unsubstituted C2-C6 alkanoyl, and wherein the "substituted" means having one or more substituents selected from the group consisting of: halogen, C1-C3 alkyl, C1-C3 haloalkyl, nitro, hydroxyl, amino and cyano.

Moreover, in the formula I and formula II, except existing chirality, various other chiral centers are in R type or S type;

In, an embodiment, R2 is Cl, and R3 is F; or R2 is Cl, and R3 is Cl; or R2 is F and R3 is Cl. In an embodiment, the optical isomer includes tautomers, cis-trans isomers, conformers, meso compounds and optical isomers in enantiomeric or diastereomeric relationship.

In an embodiment, the compound is selected from the group consisting of

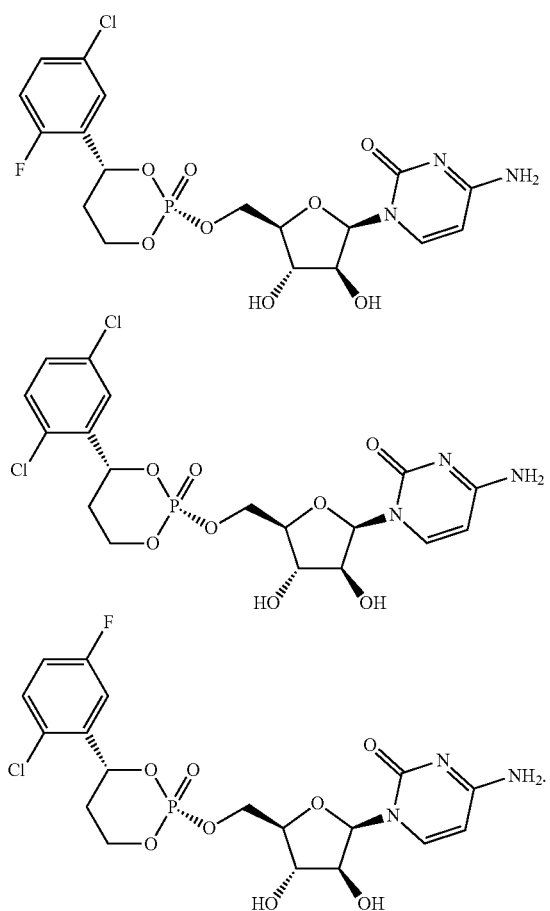

In an embodiment, salts of compounds represented by the formula I and the formula II are pharmaceutically acceptable salts formed by the compounds represented by the formula I and the formula II and an inorganic acid or an organic acid, or the salts of the compounds represented by the formula I and the formula II are pharmaceutically acceptable salts formed by the reaction between compounds represented by the formula I and the formula II and a base. The compounds represented by the formula I and the formula II or salts thereof are amorphous substances or crystals.

A second aspect of the present disclosure provides a pharmaceutical composition, wherein the pharmaceutical composition includes a therapeutically effective amount of the compound as described in the first aspect of the present disclosure, or an optical isomer, a pharmaceutically acceptable salt, a hydrate or a solvate thereof and a pharmaceutically acceptable adjuvant, a diluent or a carrier.

A third aspect of the present disclosure provides use of the compound as described in the first aspect of the present disclosure, or an optical isomer, a pharmaceutically acceptable salt, a hydrate or a solvate thereof, for preparation of a pharmaceutical composition for treating and/or preventing cancers, especially liver cancer. A fourth aspect of the present disclosure provides a method for preparing the compound represented by the formula I as described in the first aspect of the present disclosure, wherein the method includes following steps:

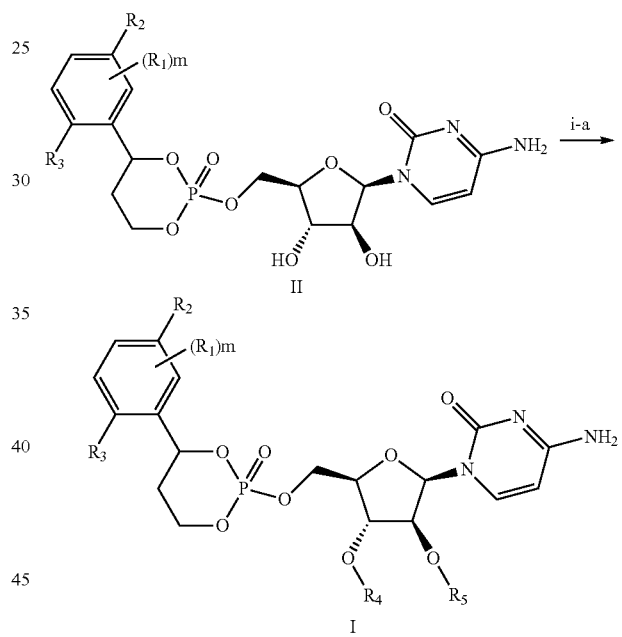

(i-a) Making a compound of the formula II undergo reaction with an acid, an acyl chloride, and a haloalkyl in an inert solvent to form a compound of the formula I.

In the formulas, each group is as defined above.

In an embodiment, in the step (i-a), the reagent is selected from the group consisting of: dicyclohexylcarbodiimide (DCC), triethylamine, N,N-diisopropylethylamine or a combination thereof, and is preferably DCC and triethylamine.

In an embodiment, in the step (i-a), the inert solvent is selected from the group consisting of: N,N-dimethylformamide, dichloromethane, tetrahydrofuran or a combination thereof, and is preferably N,N-dimethylformamide and dichloromethane solvent.

In an embodiment, a reaction temperature in the step (i-a) is 0-100° C. (preferably around 25±5° C.).

In an embodiment, reaction time of deprotection reaction in the step is 0.5-24 hours, and preferably 0.5-8 hours.

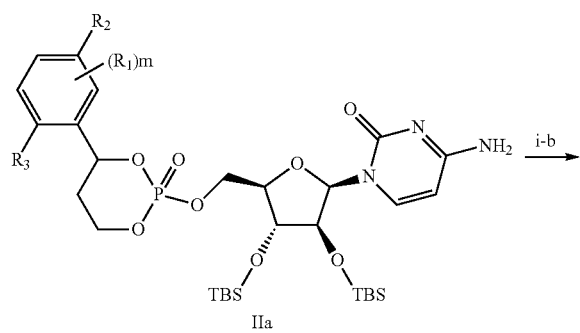

IIa

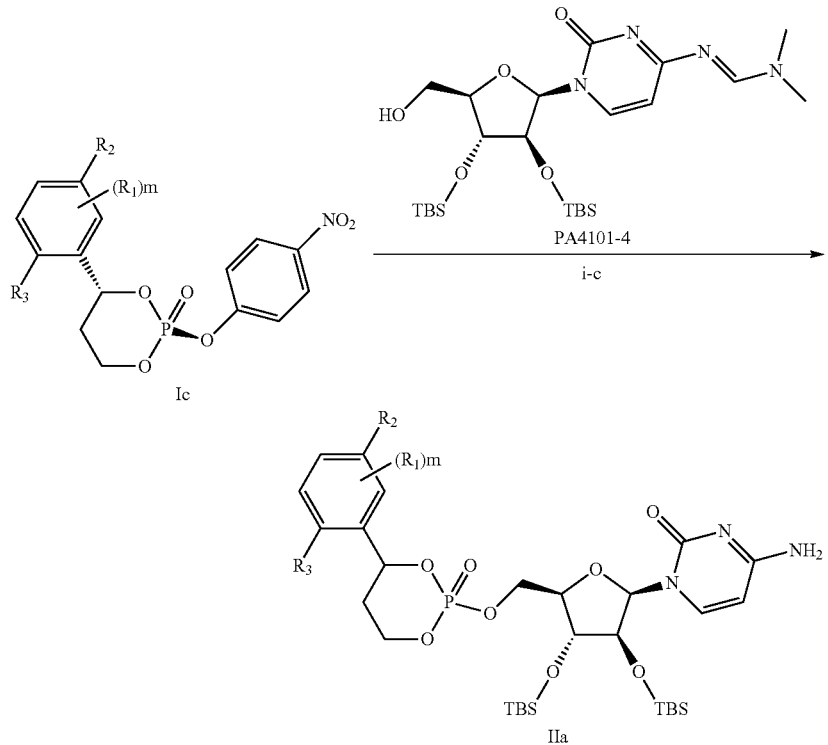

glacial acetic acid, dilute hydrochloric acid or a combination thereof, and is preferably hydrochloric alcohol solution and TBAF.

In an embodiment, in the step (i-b), the inert solvent is selected from the group consisting of: N,N-dimethylformamide, tetrahydrofuran or a combination thereof, and is preferably tetrahydrofuran solvent.

In an embodiment, a reaction temperature in the step (i-b) is −50-30° C. (preferably around 25±5° C.).

In an embodiment, reaction time of deprotection reaction in the step (i-b) is 0.5-6 hours, preferably 0.5-3 hours, and more preferably 0.5-2 hours.

In an embodiment, the compound of formula IIa is prepared by a following method:

-continued

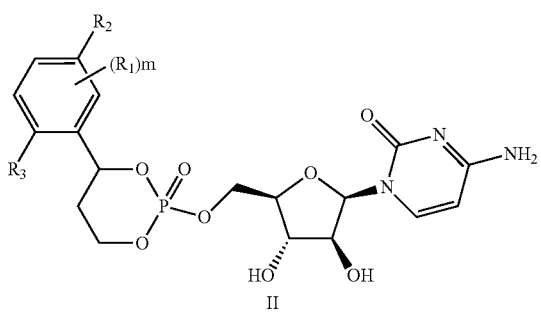

II (i-b) Removing TBS from a compound of the formula IIa in an inert solvent to form the compound of the formula II;

In an embodiment, in the step (i-b), a TBS removal reagent is selected from the group consisting of: TBAF, (i-c) Making a compound of the formula Ic undergo substitution reaction with PA4101-4 in an inert solvent to obtain the compound of formula IIa;

In another preferred embodiment, in the step (i-c), the reaction is carried out in the presence of a Grignard reagent; and preferably, the Grignard reagent is selected from the group consisting of: tert-butylmagnesium chloride (t-BuMgCl).

In an embodiment, the substitution reaction in the step (i-c) is carried out at −50-30° C. (preferably around 25±5° C.).

In an embodiment, reaction time of the substitution reaction in the step is 1-72 hours, preferably 3-48 hours, and more preferably 6-24 hours.

In an embodiment, the inert solvent in the step (i-c) is selected from the group consisting of: N,N-dimethylformamide, tetrahydrofuran or a combination thereof, and is preferably tetrahydrofuran solvent.

It should be understood that within the scope of the present disclosure, various technical features of the present disclosure described above and various technical features specifically described below (e.g., in the examples) may be combined with each other so as to form new or preferred technical solutions, which are not repeated herein one by one due to space limitation.

Notes:

ARA-C: cytarabine, 4-amino-1-B-D-arabinofuranosyl-2 (1H)-pyrimidone (CAS: 147-94-4)

ARA-CMP: 4-amino-1-B-D-5'-arabinofuranosyl monophosphate-2(1H)-pyrimidinone

DETAILED DESCRIPTION OF EMBODIMENTS

Through long-term and in-depth research, by screening and researching a large number of compounds, the inventors found for the first time that a class of compounds of formula I and formula II having specific structures (wherein site 2 and site 5 of benzene ring moiety are specific halogens) surprisingly had quite excellent activity against liver cancer, significantly improved liver delivery property and significantly reduced toxic and side effects. Based on the above findings, the inventors completed the present disclosure.

Terms

As used herein, the term "C1-C6 alkyl" refers to a straight or branched chain alkyl having 1~6 carbon atoms, for example, methyl, ethyl, propyl, isopropyl, butyl, isobutyl, see butyl, tert-butyl, or similar groups.

As used herein, the term "C2-C6 alkanoyl" refers to a substituent shaped like a structure "straight or branched chain alkyl-carbonyl having 1~6 carbon atoms", for example, acetyl, propionyl, butyryl, or similar groups.

As used herein, the term "C1-C6 alkylamino" refers to a substituent, shaped like a structure "straight or branched chain alkyl-amino having 1~6 carbon atoms", for example, methylamino, dimethylamino, ethylamino, propylamino diethylamino, or similar groups.

The term "halogen" refers to F, Cl, Br and I.

In the present disclosure, the terms "containing", "including" or "comprising" mean that various ingredients may be used together in a mixture or composition of the present disclosure. Thus, the terms "consisting essentially of . . . " and "consisting of . . . " are encompassed by the term "containing".

In the present disclosure, the term "pharmaceutically acceptable" ingredient refers to a substance that is suitable for humans and/or animals without undue adverse side effects (such as toxicity, irritation and allergic response), i.e., at a reasonable benefit/risk ratio.

In the present disclosure, the term "effective amount" refers to an amount of a therapeutic agent for treatment, amelioration or prevention of a target disease or condition, or an amount that exhibits a detectable therapeutic or prophylactic effect. A precise effective amount for a certain subject depends upon the body size and health condition of the subject, the nature and extent of the disorder, and a therapeutic agent and/or a combination of therapeutic agents selected for administration. Therefore, it is not useful to specify an accurate effective amount in advance. However, for a given condition, routine experimentation can be, used to determine the effective amount, which can be determined by clinicians.

Herein, unless otherwise specified, the term "substituted" means that one or more hydrogen atoms on a group are substituted with a substituent selected from the group consisting of: halogen, C1-C3 alkyl, C1-C3 haloalkyl, nitro, hydroxyl, amino and cyano.

Unless otherwise specified, all compounds appearing in the present disclosure are intended to include all possible optical isomers, such as single chiral compounds, or a mixture (i.e., racemate) of various different chiral compounds. In all compounds of the present disclosure, each chiral carbon atom may optionally be in R configuration or S configuration, or a mixture of R configuration and S configuration.

As used herein, the term "compound of the present disclosure" refers to compounds represented by formula I and formula II. The term also includes various crystalline forms, pharmaceutically acceptable salts, hydrates or solvates of the compounds of the formula I and the formula II.

As used herein, the term "pharmaceutically acceptable salt" refers to a salt formed by the compound of the present disclosure and an acid or a base suitable for acting as a pharmaceutical. The pharmaceutically acceptable salt includes inorganic salts and organic salts. One class of preferred salts are slats that formed by the compound of the present disclosure and an acid. Acids suitable for forming salts include, but are not limited to: inorganic acids such as hydrochloric acid, hydrobromic acid, hydrofluoric acid, sulfuric acid, nitric acid, and phosphoric acid, organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, phenylmethanesulfonic acid, and benzenesulfonic acid; and acidic amino acids such as aspartic acid and glutamic acid.

Some compounds in the present disclosure may be crystallized or recrystallized using water or various organic solvents, in which case various solvates may be formed. Solvates in the present disclosure include stoichiometric solvates such as hydrates, as well as compounds formed when prepared by the low pressure sublimation drying, method and containing a variable amount of water.

It should be understood that there may be a variety of thermodynamically stable isomers after the compound of the present disclosure is prepared, such as tautomers, conformers, meso compounds and optical isomers in enantiomeric or diastereomeric relationship, and the above variations will be apparent to those skilled in the art after reading the present disclosure.

Compound of Formula I and Preparation Thereof

In order to provide a high-efficiency and low-toxicity liver delivery prodrug capable of enabling anti-cancer nucleotide drugs to be released intensively in hepatocytes through a liver delivery mechanism, the inventors prepared a compound of formula I:

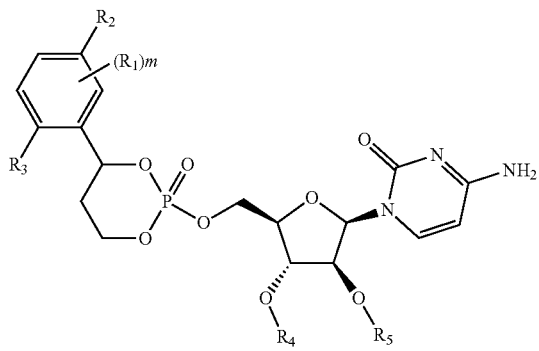

wherein
each R1 is independently selected from the group consisting of halogen, nitro, hydroxyl, amino, cyano, substituted or unsubstituted C1-C6 alkyl, substituted or unsubstituted C3-C8 cycloalkyl, substituted or unsubstituted C1-C6 alkoxy, substituted or unsubstituted C1-C6 alkylamino, substituted or unsubstituted C1-C6 carboxyl, substituted or unsubstituted C1-C6 ester group, substituted or unsubstituted C2-C6 alkanoyl, and substituted or unsubstituted. C2-C6 alkylamido, wherein the "substituted" means having one or more substituents selected from the group consisting of: halogen, C1-C3 alkyl, C1-C3 haloalkyl, nitro, hydroxy, amino, and cyano;

m is 0, 1, 2, or 3;

R2 and R3 are each independently halogen (F or Cl);

R4 and R5 are each independently selected from the group consisting of: hydrogen, substituted or unsubstituted C1-C6 alkyl, substituted or unsubstituted C3-C8 cycloalkyl, substituted or unsubstituted C1-C6 ester group, and substituted or unsubstituted C2-C6 alkanoyl, wherein the "substituted" means having one or more substituents selected from the group consisting of: halogen, C1-C3 alkyl. C1-C3 haloalkyl, nitro, hydroxyl, amino and cyano.

Moreover, in the formula I, except existing chirality, various other chiral centers are in R type or S type;

The compound may be a racemate, or an optical isomer, both of which have certain liver cancer therapeutic activity. Preferably, the compound of the formula I has a structure selected from the group consisting of:

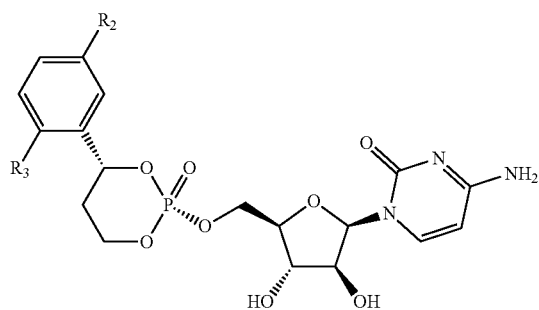

In an embodiment, the P2 and aromatic group at site 4 of the phosphate ring structure are cis with each other, and the P2 is in R configuration, and the C4 is in S type.

In an embodiment, R2 is Cl, and R3 is F; or R2 is Cl, and R3 is Cl; or R2 is F and R3 is Cl.

In an embodiment, the optical isomer includes tautomers, cis-trans isomers, conformers, meso compounds and optical isomers in enantiomeric or diastereomeric relationship.

In an embodiment, the compound is selected from the following group:

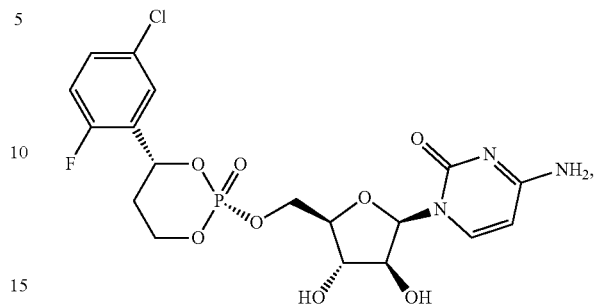

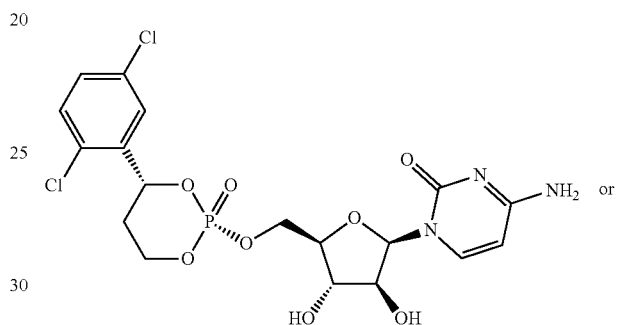

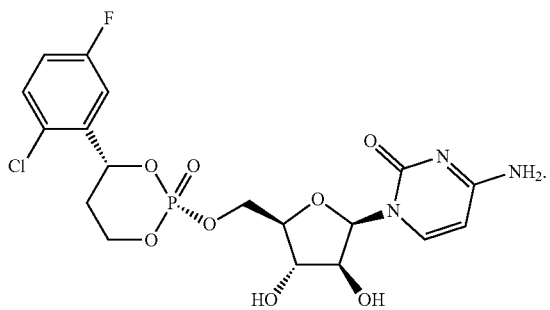

A Method for Preparing the Compound of the General Formula I is as Follows:

In a tetrahydrofuran solution, a compound PA4101-4 is added, then t-butylmagnesium chloride is added dropwise at 0° C., followed by reaction for 30 minutes, then an Ic compound is added all at once, followed by reaction overnight, quenching, and purification by silica gel chromatographic column to obtain an intermediate IIa. IIa is added to a hydrochloric alcohol solution, and a protecting group TBS is removed to obtain a compound of general formula II, II reacts with acid, acyl chloride, or haloalkyl to obtain the compound of the general formula I.

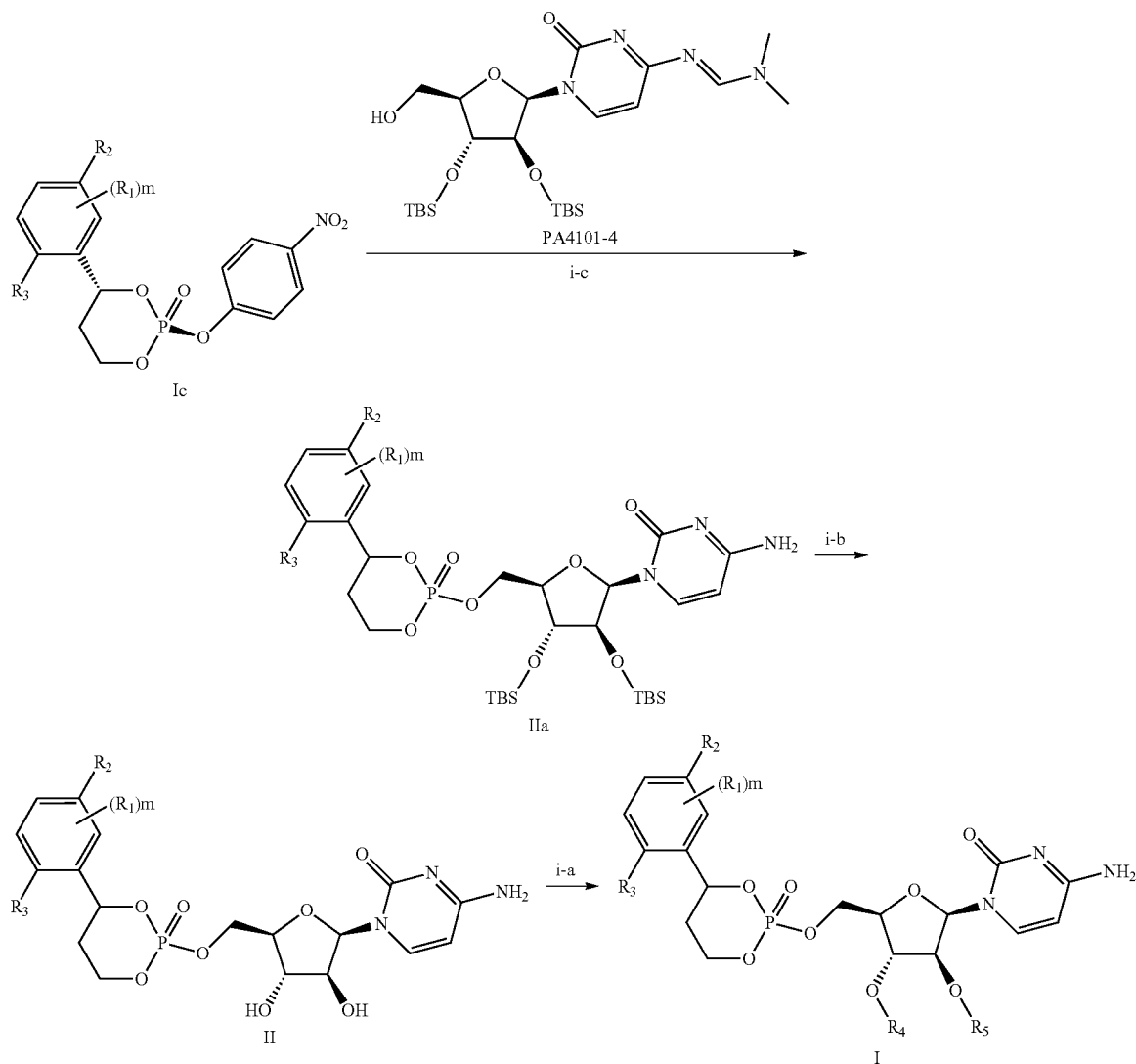

In the above, each reactant may be obtained by commercially available routes, and may also be prepared by conventional methods in the art using commercially available raw materials.

Pharmaceutical Composition and Method of Administration

As the compounds of the present disclosure have excellent inhibitory activity on liver cancer, the compound of the present disclosure and various crystal forms thereof, pharmaceutically acceptable inorganic or organic salts, hydrates or solvates, and pharmaceutical compositions containing the compound of the present disclosure acting as a main active ingredient may be used for treatment, prevention and alleviation of cancers, especially liver cancer and related symptoms thereof.

The pharmaceutical composition of the present disclosure contains the compound of the present disclosure, or a pharmacologically acceptable salt thereof and pharmacologically acceptable excipient or carrier within a safe and effective amount range. In the above, "safe and effective amount" means that the amount of the compound is sufficient to significantly improve the condition without causing severe side effects. Generally, the pharmaceutical composition contains 0.1-1000 mg of the compound of the present disclosure/dose, more preferably 0.5~500 mg of the compound of the present disclosure/dose. Preferably, "one dose" is one capsule, or tablet.

"Pharmaceutically acceptable carrier" refers to one or more compatible solids or liquid fillers or gel substances, which are suitable for human use and must be of sufficient purity and sufficiently low toxicity. "Compatibility" herein means that various components in the composition can be intermingled with the compound of the present disclosure and with each other, without significantly reducing the efficacy of the compound. Examples of pharmaceutically acceptable carrier moieties include celluloses and derivatives thereof (such as sodium carboxymethylcellulose, sodium ethylcellulose, and cellulose acetate), gelatin, talc, solid lubricants (such as stearic acid and magnesium stearate), calcium sulfate, vegetable oils (such as soy oil, sesame oil, peanut oil, and olive oil), polyols (such as propylene glycol, glycerol, mannitol, and sorbitol), emulsifiers (such as Tween®), wetting agents (such as lauryl sodium sulfate), colorants, flavoring agents, stabilizers, antioxidants, preservatives, pyrogen-free water and so on.

A mode of administration of the compound or pharmaceutical composition of the present disclosure is not particularly limited, and representative modes of administration include (but are not limited to) oral, rectal, parenteral (intravenous, intramuscular or subcutaneous), and topical administration. A particularly preferred mode of administration is oral administration.

Solid dosage forms used for oral administration include capsule, tablet, pill, powder and, granule. In these solid dosage forms, the active compound is mixed with at least one conventional inert excipient (or carrier), such as sodium citrate or dicalcium phosphate, or mixed with following ingredients: (a) a filler or a compatibilizer, for example, starch, lactose, sucrose, glucose, mannitol and silicic acid; (b) a binder, for example, hydroxymethyl cellulose, alginate, gelatin, polyvinylpyrrolidone, sucrose and Arabic gum; (c) a humectant, for example, glycerol; (d) a disintegrant, for example, agar, calcium carbonate, potato starch or tapioca starch, alginic acid, certain complex silicates, and sodium carbonate; (e) a slow solvent, for example, paraffin; (f) an absorption accelerator, for example, quaternary amine compounds; (g) a wetting agent, for example, cetyl alcohol and glyceryl monostearate; (h) an adsorbent, for example, kaolin; and (i) a lubricant, for example, talc, calcium stearate, magnesium stearate, solid polyethylene glycol, lauryl sodium sulfate, or mixtures thereof. In the capsule, tablet and pill, the dosage forms may also contain a buffer.

Solid dosage forms such as tablet, sugar pill, capsule, pill and granule can be prepared using coatings and shell materials such as enteric coatings and other materials commonly known in the art. They may contain an opacifying agent, and the active compound or compound in such composition may be released in a certain part within the digestive tract in a delayed, manner. Examples of embedding components that may be employed are polymeric substances and waxy substances. If necessary, the active compound may also form a microcapsule form with one or more of the above excipients.

Liquid dosage forms used for oral administration include pharmaceutically acceptable emulsion, solution, suspension, syrup or tincture. In addition to the active compound, the liquid dosage form may contain an inert diluent conventionally used in the art, such as water or other solvents, a solubilizer and an emulsifier, for example, ethanol, isopropanol, ethyl carbonate, ethyl acetate, propylene glycol, 1,3-butanediol, dimethylformamide and oils, in particular cottonseed oil, peanut oil, maize germ oil, olive oil, castor oil and sesame oil, or a mixture of these substances.

In addition to these inert diluents, the composition may also contain an adjuvant such as wetting agent, emulsifier, suspending agent, sweetener, corrigent and fragrance.

In addition to the active compounds, the suspension may contain a suspending agent, for example, ethoxylated isooctadecanol, polyoxyethylene sorbitol and sorbitan ester, microcrystalline cellulose, aluminum methoxide and agar, or a mixture of these substances.

A composition used for parenteral injection may contain a physiologically acceptable sterile aqueous or anhydrous solution, dispersion liquid, suspension or emulsion, and sterile powder for redissolution into sterile injectable solution or dispersion liquid. Suitable aqueous and non-aqueous carrier, diluent, solvent or excipient includes water, ethanol, polyol and suitable mixtures thereof.

Dosage forms of the compound of the present disclosure used for topical administration include ointment, powder, patch, spraying agent and inhalant. The active ingredients are mixed together, under sterile conditions, with a physiologically acceptable carrier and any preservative, buffer, or propellant that may be needed as necessary.

The compound, of the present disclosure may be administered alone or in combination with other pharmaceutically acceptable compounds.

When the pharmaceutical composition is used, a safe and effective amount of the compound of the present disclosure is applied to a mammal (such as a human) in need of treatment, wherein the dose when administered is a pharmaceutically recognized effective dosage of administration, and for a person having a body weight of 60 kg, the daily dosage of administration is usually 0.2~1000 mg, preferably 0.5~500 mg. Of course, factors such as the route of administration and the health condition of the patient should also be taken into account for the specific dosage, which is within the skill range of skilled physicians.

Main Advantages of the Present Disclosure Include:

(1) With high liver delivery property, the compound can only be specifically catalyzed by CYP3A in the cytochrome P450 isoenzyme family in hepatocytes to generate active molecules, and the active molecules carry high negative charges and are not easy to be discharged out of the liver, therefore, the concentration in the liver is higher, such that the liver delivery effect is achieved.

(2) The activity is high, and due to the liver delivery property, more drugs exist in the liver, and the anti-cancer activity can also be greatly improved.

(3) The toxic and side effects are low: for an equivalent dosage of prodrug, a quite small amount is metabolized into active molecules outside the liver, therefore, the toxicity to major organs such as kidney and bone marrow is greatly reduced.

The present disclosure is further illustrated below in combination with specific examples. It should be understood that these examples are merely used to illustrate the present disclosure, rather than limiting the scope of the present disclosure. The experimental method, of which no specific conditions are specified in the following examples, are generally carried out under conventional conditions or conditions recommended by manufacturers, Unless otherwise specified, percentages and parts are calculated by weight.

Example 1 PA4101

Synthesis Route:

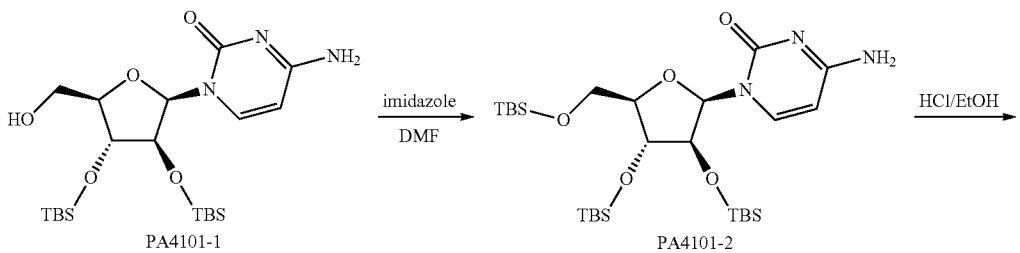

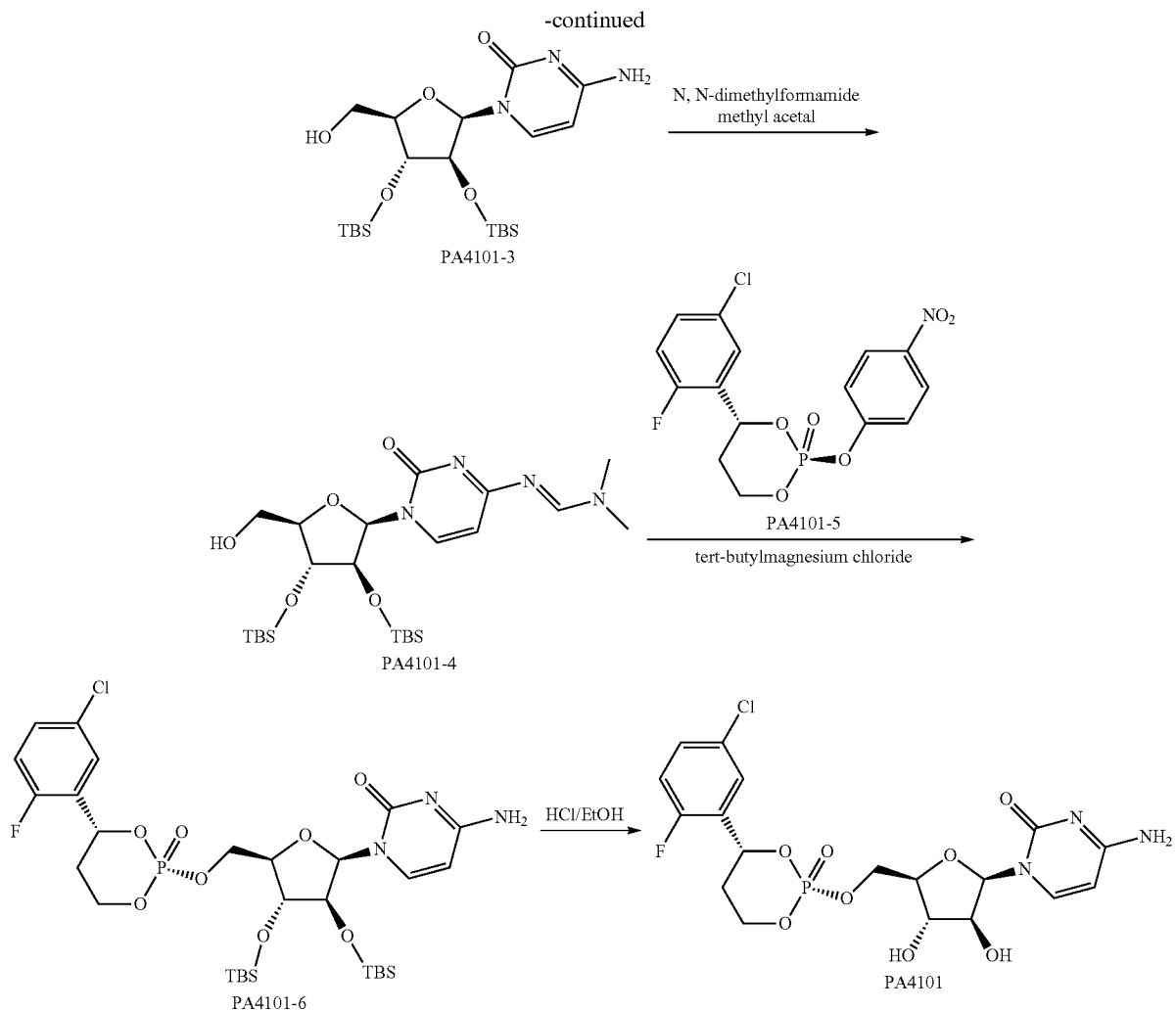

Experimental Section:

Step 1) Synthesis of Compound PA4101-2:

dissolving a compound PA4101-1 (Cytarbine, 9.5 g, 39 mmol) and imidazole (18 g, 264 mmol) in DMF (100 mL), adding 4-dimethylaminopyridine ((DMAP, 3.8 g, 31 mmol), adding tert-butyldimethylsilyl chloride (TBSCl, 30 g, 198 mmol) slowly in an ice bath, under nitrogen protection, carrying out reaction at 63° C. while stirring overnight, after completing the reaction, adding a reaction solution slowly to water (400 mL), followed by extraction with ethyl acetate (3×300 mL), washing by saturated brine, drying over anhydrous sodium sulfate, followed by filtration, spin-drying, and separation and purification by silica gel chromatographic column to obtain PA4101-2 (20.6 g), with yield of 90%.

Step 2) Synthesis of Compound PA4101-3:

dissolving the compound PA4101-2 (20.6 g, 35.2 mmol) in 0.5% hydrochloric alcohol solution (610 mL), after stirring the reaction solution at room temperature for 4.5 hours (the reaction was completed according to TLC or LCMS tracing), neutralizing the reaction solution with a saturated NaHCO$_3$ solution, removing ethanol by rotary evaporation, adding water (200 mL), followed by extraction with ethyl acetate (3×200 mL), drying over anhydrous sodium sulfate followed by filtration, spin-drying, and separation and purification by silica gel chromatographic column (eluent was: PE:EA:CH3OH (V:V)=150:150:4.5) to obtain a white solid compound PA4101-3 (14.7 g), with yield of 89%.

Step 3) Synthesis of Compound PA4101-4:

dissolving the compound PA4101-3 (14.7 g, 31.2 mmol) in a pyridine solvent (50 mL), adding N,N-dimethylformamide methyl acetal (4.83 g, 40.5 mmol), carrying out reaction at room temperature while stirring overnight, and removing pyridine by rotary evaporation to obtain a crude product, and separating and purifying the crude product by silica gel chromatographic column (eluent: dichloromethane:methanol (V:V)=100:3) to obtain a white solid compound PA4101-4 (13.0 g), with yield of 79%.

Step 4) Synthesis of Compound PA4101-6:

dissolving the compound PA4101-4 (6.7 g, 12.7 mmol) in tetrahydrofuran (130 mL) under nitrogen protection, cooling the mixture in ice bath to 0° C. slowly adding 1 M tert-butylmagnesium chloride solution (50.0 mL, 50 mmol) dropwise, after completing the dropwise addition, stirring the reaction solution at room temperature for 1 hour, and cooling the reaction solution again to 0° C., adding PA4101-5 (6.4 g, 16.5 mmol), carrying out the reaction while stirring at room temperature for 12 h after completing the reaction, quenching the reaction with saturated ammonium chloride, solution (50 mL), followed by extraction with ethyl acetate (3×200 mL), washing with saturated brine, drying over anhydrous sodium sulfate, spin-drying, and separating and purifying by silica gel chromatographic column to obtain a white solid compound PA4101-6 (6.15 g), with yield of 67%.

Step 5) Synthesis of Compound PA4101:

dissolving the compound PA4101-6 (11.5 g, 16 mmol) in 12% hydrochloric alcohol solution, and carrying out reaction while stirring at room temperature overnight, after TLC showed completion of reaction, adjusting a pH value to 8-9 with aqueous ammonia, after removing ethanol by rotary evaporation, adding water (100 mL), followed by extraction with ethyl acetate (3×100 mL), washing an organic phase with saturated brine, drying over anhydrous sodium sulfate followed by filtration, spin-drying, and purification by Combiflash chromatography column to obtain a white solid PA4101 (4.5 g), with yield of 57%.

Example 2 PA4102 (Comparative Example)

Synthesis Route:

tert-butylmagnesium chloride solution (26.0 mL, 26.0 mmol) dropwise, after completing the dropwise addition, stirring the reaction solution at room temperature for 1 hour, and cooling the reaction solution again to 0° C., adding PA4102-1 (2.13 g, 6.3 mmol), stirring the mixture at room temperature overnight, after completing the reaction, quenching the reaction with saturated ammonium chloride solution (30 mL), followed by extraction with ethyl acetate (3×150 mL), washing with saturated brine, drying over anhydrous sodium sulfate, spin-drying, and separating and purifying, by silica gel chromatographic column to obtain a white solid compound PA4102-2 (0.68 g), with yield of 19.2%.

Step 2) Synthesis of Target Compound PA4102:

dissolving the compound PA4102-2 (0.68 g, 1 mmol) in 3.6% hydrochloric alcohol solution (15 ml), and carrying out reaction while stirring at room temperature overnight, after TLC showed completion of reaction, adjusting a pH value to 8-9 with aqueous ammonia, after removing ethanol by rotary evaporation, adding water (50 mL), followed by extraction

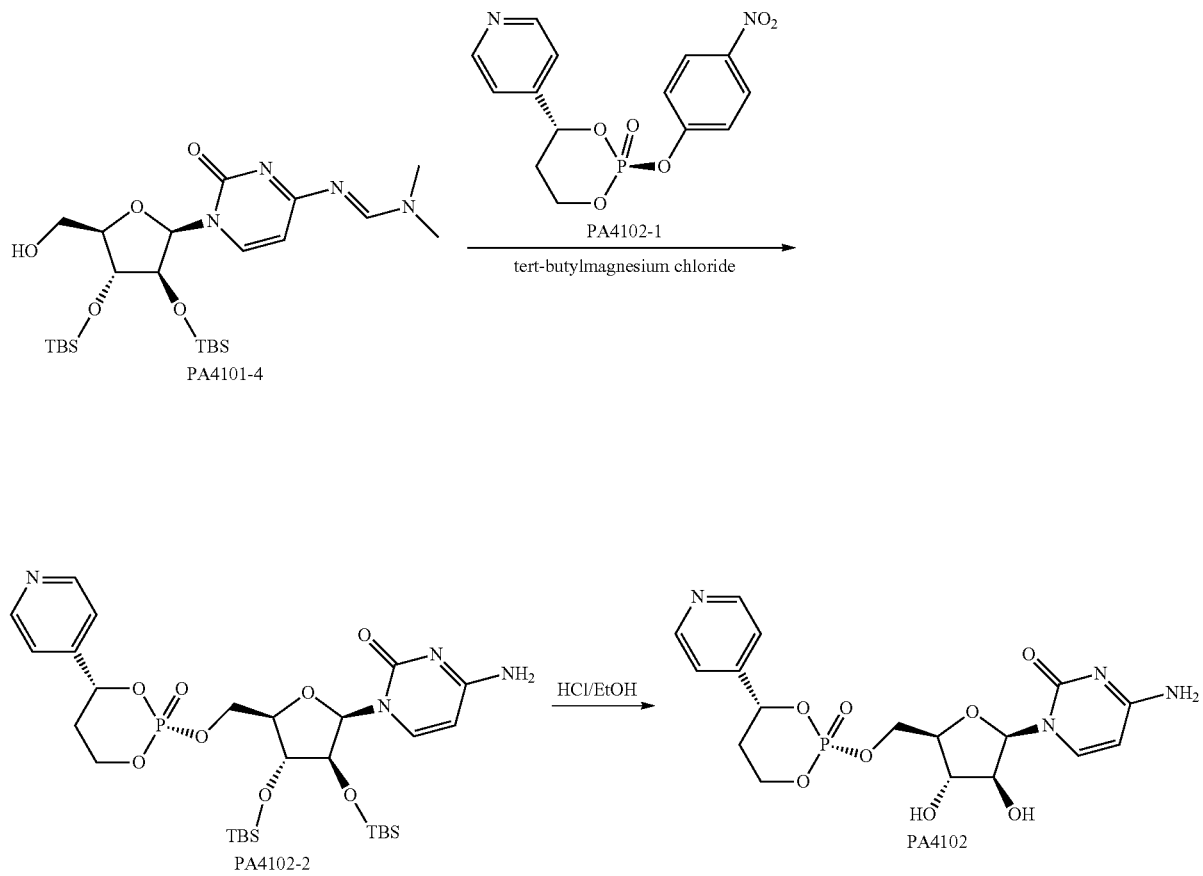

Experimental Section:

Step 1) Synthesis of Compound PA4102-2:

dissolving a compound PA4101-4 (2.79 g, 5.3 mmol) in tetrahydrofuran (60 mL) under nitrogen protection, cooling the mixture in ice bath to 0° C., slowly adding 1 M with ethyl acetate (3×50 mL), washing an organic phase with saturated brine, drying over anhydrous sodium sulfate, followed by filtration, spin-drying, and purification by Combiflash chromatography column to obtain a white solid PA4102 (300 mg), with yield of 71%.

Example 3 PA4103

Synthesis Route:

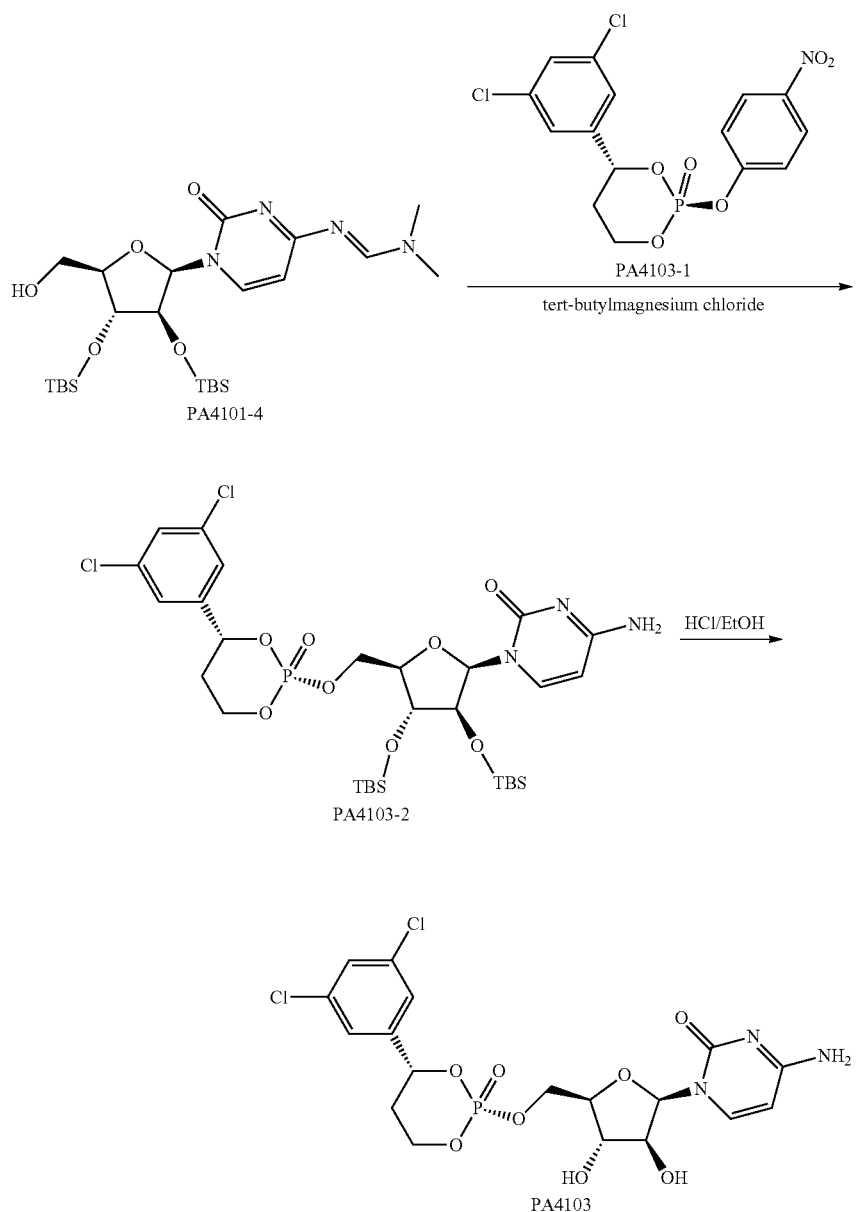

Experimental Section:

Step 1) Synthesis of Compound PA4103-2:

dissolving a compound PA4101-4 (0.37 g, 0.7 mmol) in tetrahydrofuran (10 mL) under nitrogen protection, cooling the mixture in ice bath to 0° C., slowly adding 1 M tert-butylmagnesium chloride solution (2.8 mL, 2.8 mmol) dropwise, after completing the dropwise addition, stirring the reaction solution at room temperature for 1 hour, and cooling the reaction solution again to 0° C., adding PA4103-1 (0.38 g, 0.94 mmol), stirring the mixture at room temperature overnight, after completing the reaction, quenching the reaction with saturated ammonium chloride solution (10 mL), followed by extraction with ethyl acetate (3×25 mL), washing with saturated brine, drying over anhydrous sodium sulfate, spin-drying, and separating and purifying, by silica gel chromatographic column to obtain a white solid compound PA4103-2 (0.17 g), with yield of 32%.

Step 2) Synthesis of Target Compound PA4103 dissolving the compound PA4103-2 (0.17 g, 0.28 mmol) in 3.6% hydrochloric alcohol solution (4 ml), and carrying out reaction while stirring at room temperature overnight, after TLC showed completion of reaction, adjusting a pH value to 8-9 with aqueous ammonia, after removing ethanol by rotary evaporation, adding water (15 mL), followed by extraction with ethyl acetate (3×50 mL), washing an organic phase with saturated brine, drying over anhydrous sodium sulfate, followed by filtration, spin-drying, and purification by Combiflash chromatography column to obtain a white solid PA4103 (46 mg), with yield of 39%.

Example 4 PA4104

Synthesis Route:

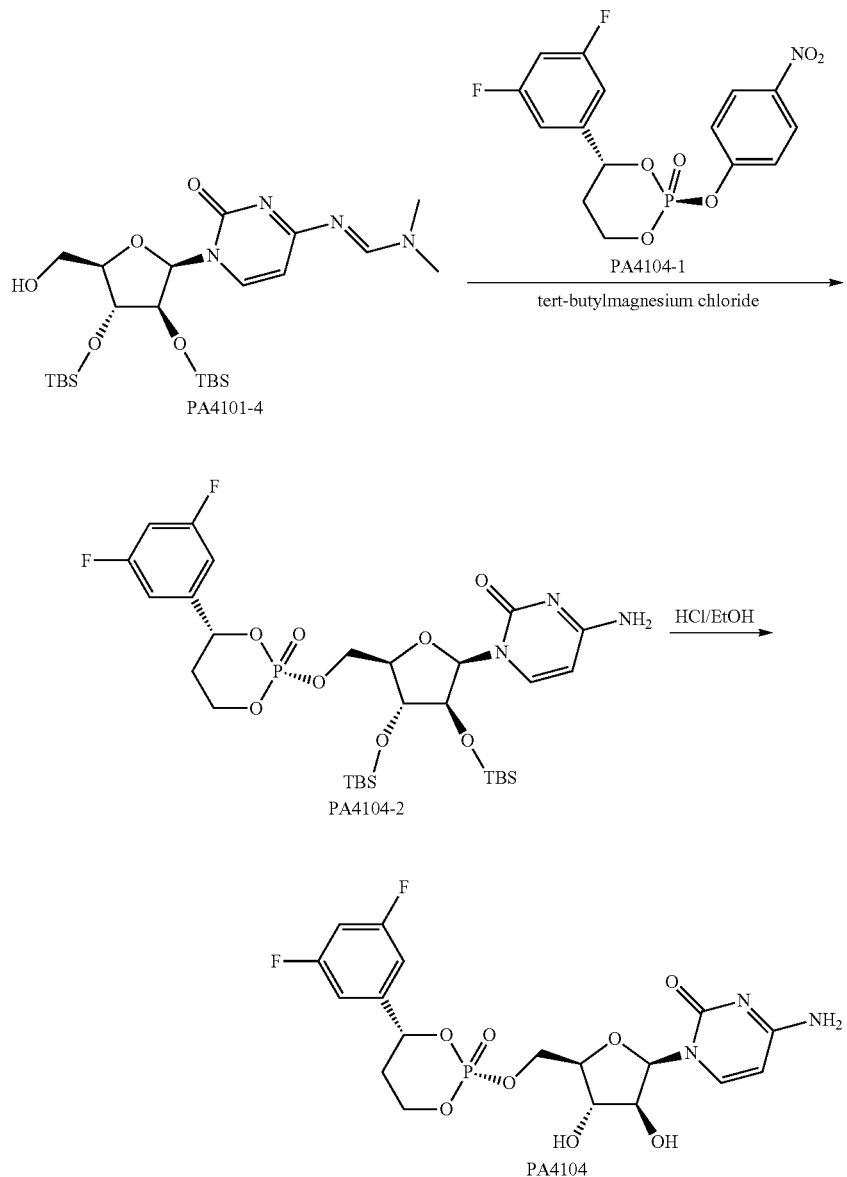

Experimental Section:

Step 1) Synthesis of Compound PA4104-2:

dissolving a compound PA4101-4 (0.37 g, 0.7 mmol) in tetrahydrofuran (10 mL) under nitrogen protection, cooling the mixture in ice bath to 0° C., slowly adding 1 M tert-butylmagnesium chloride solution (2.8 mL, 2.8 mmol) dropwise, after completing the dropwise addition, stirring the reaction solution at room temperature for 1 hour, and cooling the reaction solution again to 0° C., adding PA4104-1 (0.38 g, 0.94 mmol), stirring the mixture at room temperature overnight, after completing the reaction, quenching the reaction with saturated ammonium chloride solution (10 mL), followed by extraction with ethyl acetate (3×25 mL), washing with saturated brine, drying over anhydrous sodium sulfate, spin-drying, and separating and purifying by silica gel chromatographic column to obtain a white solid compound PA4104-2 (0.32 g), with yield of 65%.

Step 2) Synthesis of Target Compound PA4104:

dissolving the compound PA4104-2 (0.32 g, 0.46 mmol) in 3.6% hydrochloric alcohol solution (7 ml), and carrying out reaction while stirring at room temperature overnight, after TLC showed completion of reaction, adjusting a pH value to 8-9 with aqueous ammonia, after removing ethanol by rotary evaporation, adding water (25 mL), followed by extraction with ethyl acetate (3×50 mL), washing an organic phase with saturated brine, drying over anhydrous sodium sulfate, followed by filtration, spin-drying, and purification by Combiflash chromatography column to obtain a white solid PA4104 (43 mg), with yield of 20%.

Example 5 PA4145

Synthesis Route:

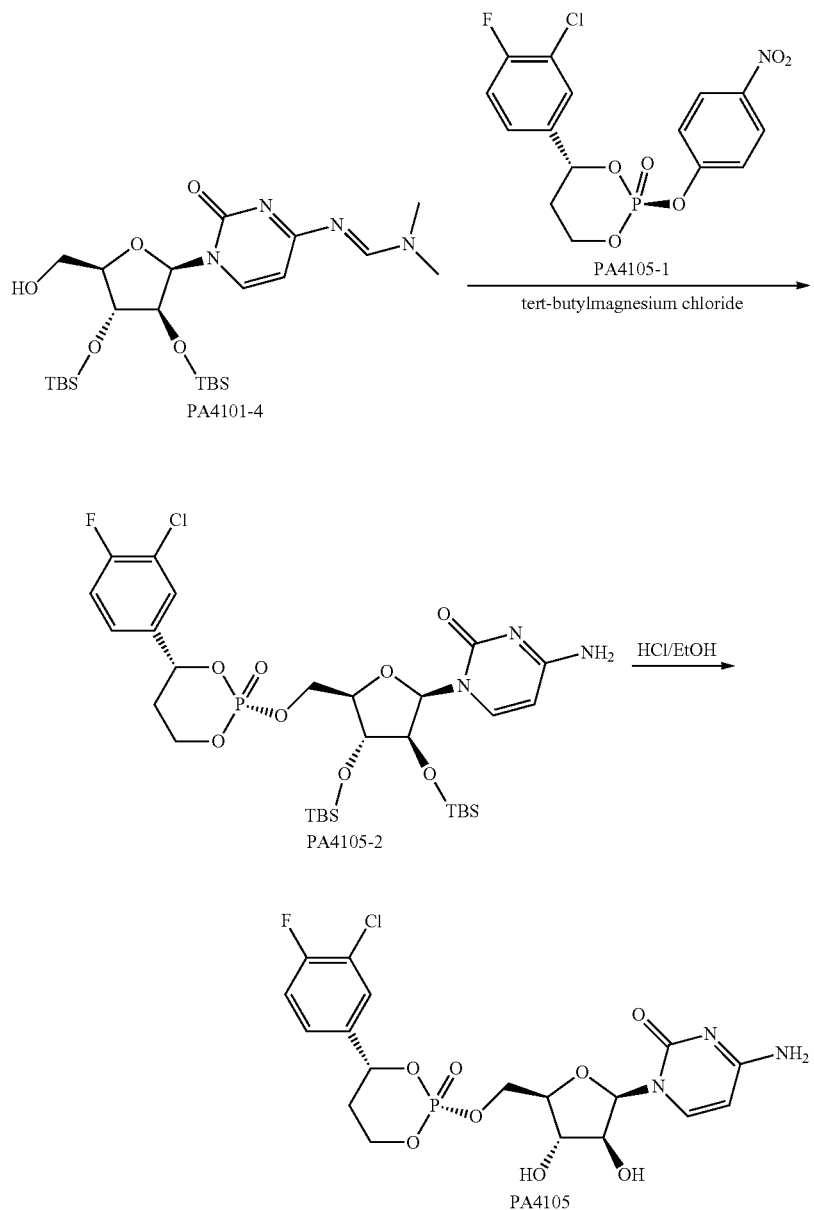

Experimental Section:

Step 1) Synthesis of Compound PA4105-2:

dissolving the compound PA4101-4 (0.33 g, 0.64 mmol) in tetrahydrofuran (10 mL) under nitrogen protection, cooling the mixture in ice bath to 0° C., slowly adding 1 M tert-butylmagnesium chloride solution (2.5 mL, 2.5 mmol) dropwise, after completing the dropwise addition, stirring the reaction solution at room temperature for 1 hour, and cooling the reaction solution again to 0° C., adding PA4105-1 (0.38 g, 0.94 mmol), stirring the mixture at room temperature overnight, after completing the reaction, quenching the reaction with saturated ammonium chloride solution (10 mL), followed by extraction with ethyl acetate (3×25 mL), washing with saturated brine, drying over anhydrous sodium sulfate, spin-drying, and separating and purifying by silica gel chromatographic column to obtain a white solid compound PA4105-2 (0.1 g), with yield of 22%.

Step 2) Synthesis of Target Compound PA4105:

dissolving the compound PA4105-2 (0.1 g, 0.14 mmol) in 3.6% hydrochloric alcohol solution (3 ml), and carrying out reaction while stirring at room temperature overnight, after TLC showed completion of reaction, adjusting a pH value to 8-9 with aqueous ammonia, after removing ethanol by rotary evaporation, adding water (10 mL), followed by extraction with ethyl acetate (3×40 mL), washing an organic phase with saturated brine, drying over anhydrous sodium sulfate, followed by filtration, spin-drying, and purification by Combiflash chromatography column to obtain a white solid PA4105 (17 mg), with yield of 24.5%.

Example 6 PA4106

Synthesis Route:

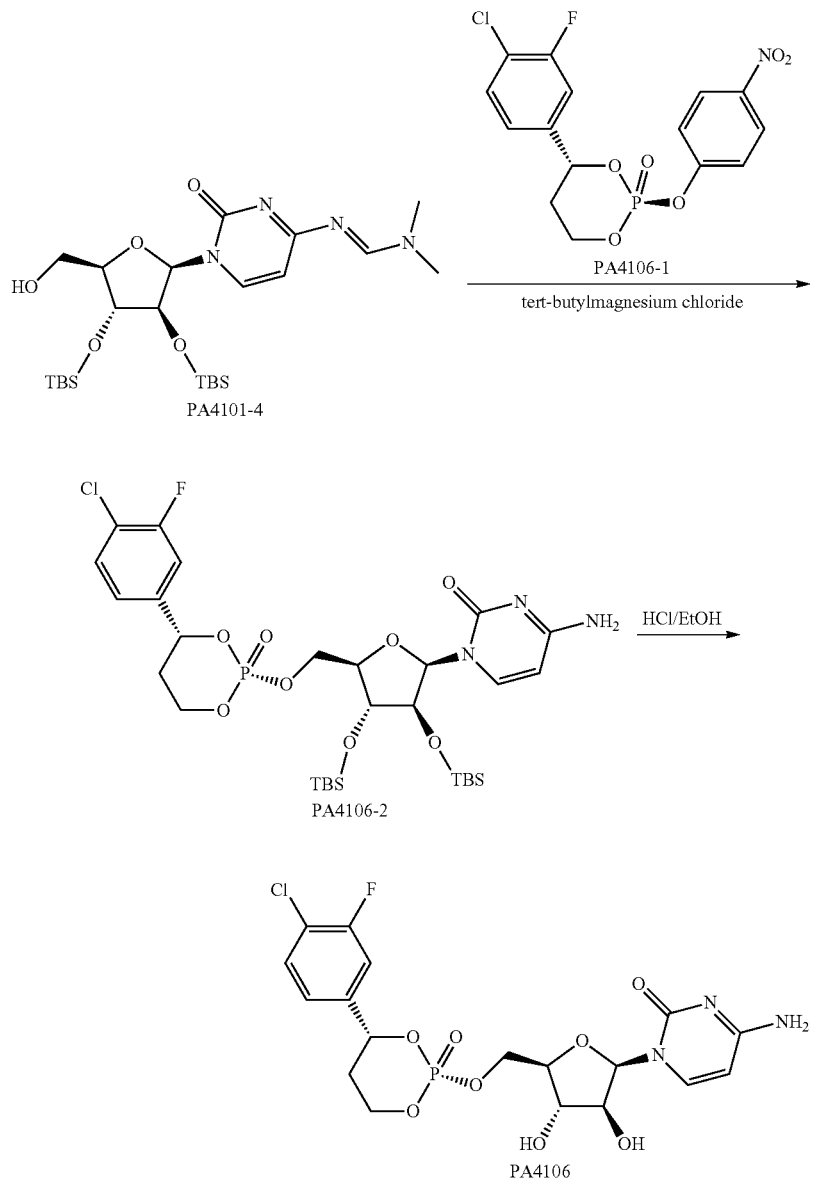

Experimental Section:

Step 1) Synthesis of Compound PA4106-2:

dissolving a compound PA4101-4 (0.33 g, 0.64 mmol) in tetrahydrofuran (10 mL) under nitrogen protection, cooling the mixture in ice bath to 0° C., slowly adding 1 M tert-butylmagnesium chloride solution (2.5 mL, 2.5 mmol) dropwise, after completing the dropwise addition, stirring the reaction solution at room temperature for 1 hour, and cooling the reaction solution again to 0° C., adding PA4106-1 (0.38 g, 0.94 mmol), stirring the mixture at room temperature overnight, after completing the reaction, quenching the reaction with saturated ammonium chloride solution (10 mL), followed by extraction with ethyl acetate (3×25 mL), washing with saturated brine, drying over anhydrous sodium sulfate, spin-drying, and separating and purifying by silica gel chromatographic column to obtain a white solid compound PA4106-2 (0.22 g), with yield of 48%.

Step 2) Synthesis of Target Compound PA4106:

dissolving the compound PA4106-2 (0.22 g, 0.3 mmol) in 3.6% hydrochloric alcohol solution (5 ml), and carrying out reaction while stirring at room temperature overnight, after TLC showed completion of reaction, adjusting a pH value to 8-9 with aqueous ammonia, after removing ethanol by rotary evaporation, adding water (20 mL), followed by extraction with ethyl acetate (3×50 mL), washing an organic phase with saturated brine, drying over anhydrous sodium sulfate, followed by filtration, spin-drying, and purification by Combiflash chromatography column to obtain a white solid PA4106 (45 mg), with yield of 30%.

Example 7 PA4107

Synthesis Route:

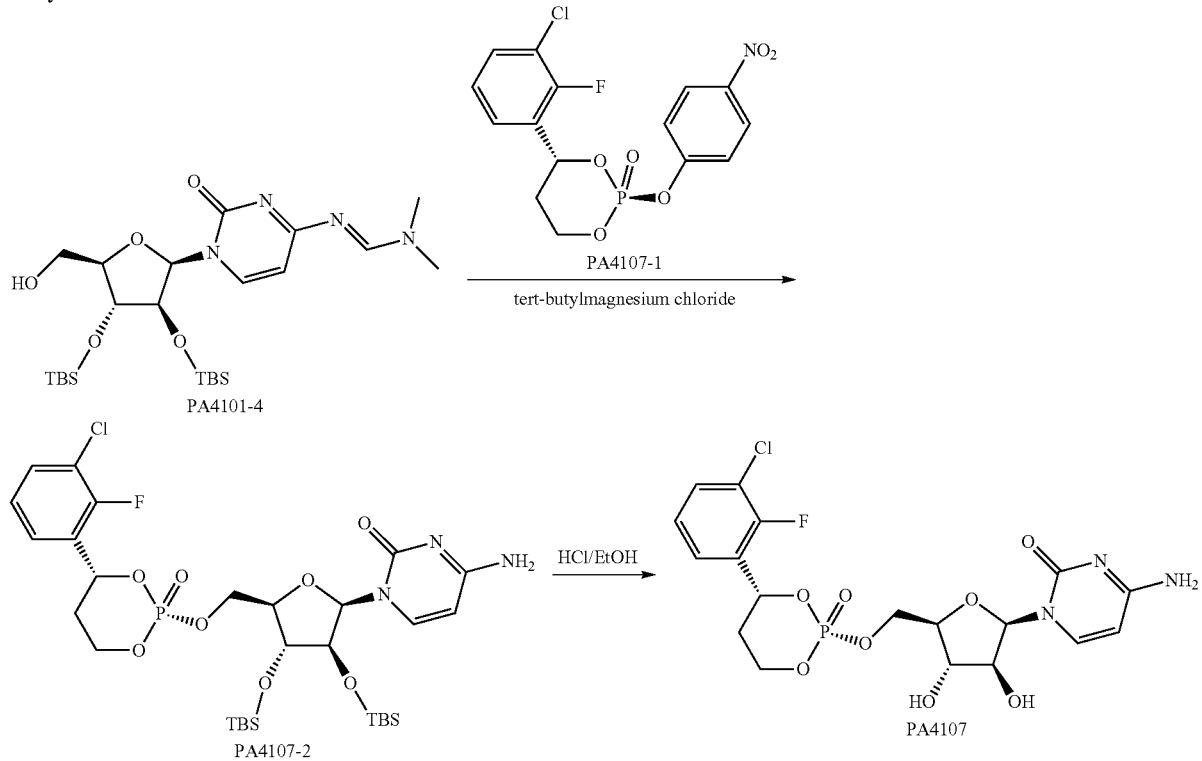

Experimental Section:

Step 1) Synthesis of Compound PA4107-2:

dissolving a compound PA4101-4 (0.35 g, 0.66 mmol) in tetrahydrofuran (10 mL) under nitrogen protection, cooling the mixture in ice bath to 0° C., slowly adding 1 M tert-butylmagnesium chloride solution (2.7 mL, 2.7 mmol) dropwise, after completing the dropwise addition, stirring the reaction solution at room temperature for 1 hour, and cooling the reaction solution again to 0° C., adding PA4107-1 (0.38 g, 0.94 mmol), stirring the mixture at room temperature overnight, after completing the reaction, quenching the reaction with saturated ammonium chloride solution (10 mL), followed by extraction with ethyl acetate (3×25 mL), washing with saturated brine, drying over anhydrous sodium sulfate, spin-drying, and separating and purifying by silica gel chromatographic column to obtain a white solid compound PA4107-2 (0.29 g), with yield of 61.7%.

Step 2) Synthesis of Target Compound PA4107:

dissolving the compound PA4107-2 (0.29 g, 0.39 mmol) in 3.6% hydrochloric alcohol solution (5 ml), and carrying out reaction while stirring at room temperature overnight, after TLC showed completion of reaction, adjusting a pH value to 8-9 with aqueous ammonia, after removing ethanol by rotary evaporation, adding water (20 mL), followed by extraction with ethyl acetate (3×50 mL), washing an organic phase with saturated brine, drying over anhydrous sodium sulfate, followed by filtration, spin-drying, and purification by Combiflash chromatography column to obtain a white solid PA4107 (90 mg), with yield of 47%.

Example 8 PA4108

Synthesis Route:

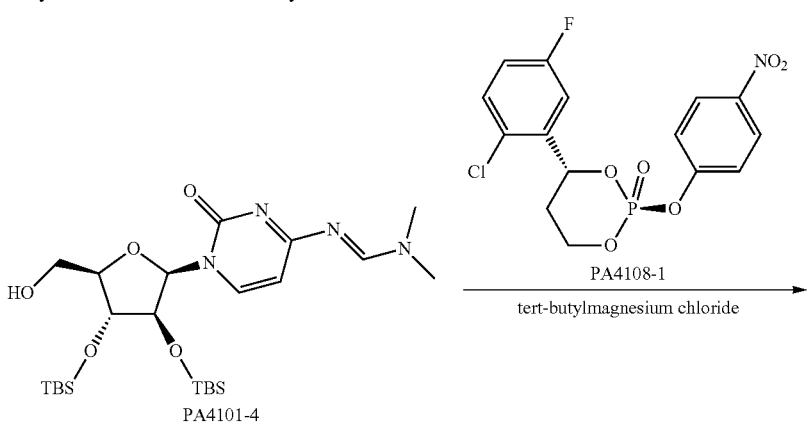

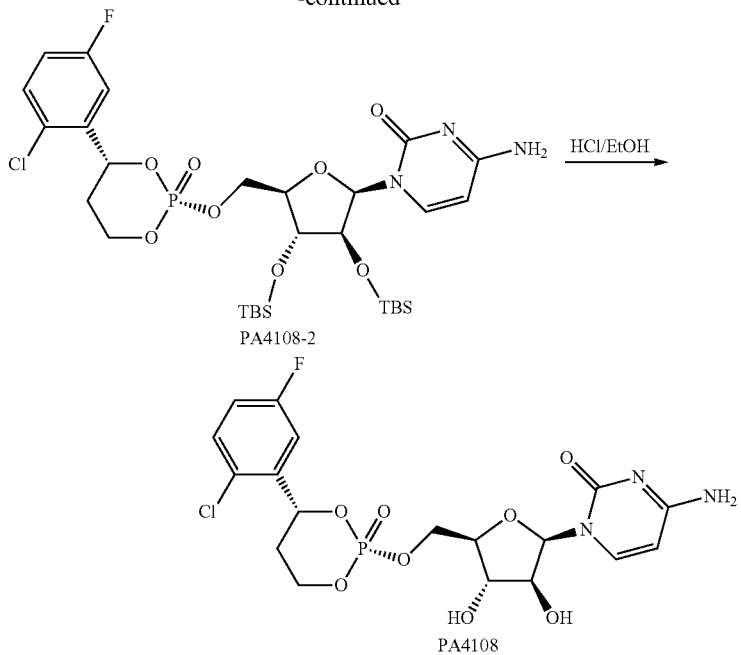
PA4108-2

PA4108

Experimental Section:

Step 1) Synthesis of Compound PA4108-2:

dissolving a compound PA4101-4 (380 mg, 0.72 mmol) in tetrahydrofuran (10 mL) under nitrogen protection, cooling the mixture in ice bath to 0° C., slowly adding 1 M tert-butylmagnesium chloride solution (3 mL, 3 mmol) dropwise, after completing the dropwise addition, stirring the reaction solution at room temperature for 1 hour, and cooling the reaction solution again to 0° C., adding PA4108-1 (0.32 g, 0.86 mmol), stirring the mixture at room temperature overnight, after completing the reaction, quenching the reaction with saturated ammonium chloride solution (15 mL), followed by extraction with ethyl acetate (3×150 mL), washing with saturated brine, drying over anhydrous sodium sulfate, spin-drying, and separating and purifying by silica gel chromatographic column to obtain a white solid compound PA4108-2 (140 mg), with yield of 27%.

Step 2) Synthesis of Target Compound PA4108:

dissolving the compound PA4108-2 (140 mg, 0.19 mmol) in 3.6% hydrochloric alcohol solution (3 ml), and carrying out reaction while stirring at room temperature overnight, after TLC showed completion of reaction, adjusting a pH value to 8-9 with aqueous ammonia, after removing ethanol by rotary evaporation, adding water (50 mL), followed by extraction with ethyl acetate (3×50 mL), washing an organic phase with saturated brine, drying over anhydrous sodium sulfate, followed by filtration, spin-drying, and purification by Combiflash chromatography column to obtain a white solid PA4108 (35 mg), with yield of 36%.

Example 9 PA4109

Synthesis Route:

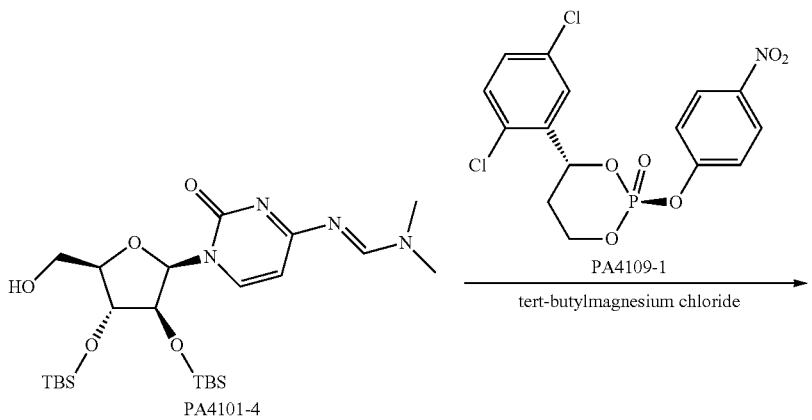

-continued

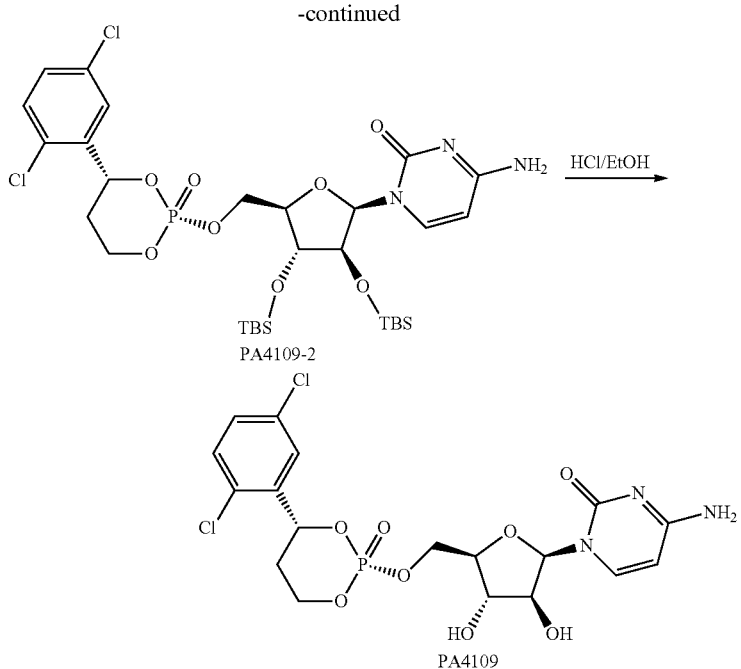

PA4109-2

HCl/EtOH

PA4109

Experimental Section:

Step 1) Synthesis of Compound PA4109-2:

dissolving a compound PA4101-4 (380 mg, 0.72 mmol) in tetrahydrofuran (10 mL) under nitrogen protection, cooling the mixture in ice bath to 0° C., slowly adding 1 M tert-butylmagnesium chloride solution (3 mL, 3 mmol) dropwise, after completing the dropwise addition, stirring the reaction solution at room temperature for 1 hour, and cooling the reaction solution again to 0° C., adding PA4109-1 (350 mg 0.86 mmol), stirring the mixture at room temperature overnight, after completing the reaction, quenching the reaction with saturated ammonium chloride solution (30 mL), followed by extraction with ethyl acetate (3×150 mL) washing with saturated brine, drying over anhydrous sodium sulfate, spin-drying, and separating and purifying by silica gel chromatographic column to obtain a white solid compound PA4109-2 (310 mg), with yield of 58.4%.

Step 2) Synthesis of Target Compound PA4109:

dissolving the compound PA4109-2 (310 mg, 0.42 mmol) in 3.6% hydrochloric alcohol solution (3 ml), and carrying out reaction while stirring at room temperature overnight, after TLC showed completion of reaction, adjusting a pH value to 8-9 with aqueous ammonia, after removing ethanol by rotary evaporation, adding water (50 mL), followed by extraction with ethyl acetate (3×50 mL), washing an organic phase with saturated brine, drying over anhydrous sodium sulfate, followed by filtration, spin-drying, and purification by Combiflash chromatography column to obtain a white solid PA4109 (110 mg), with yield of 52%.

Example 10 PA4110

Synthesis Route:

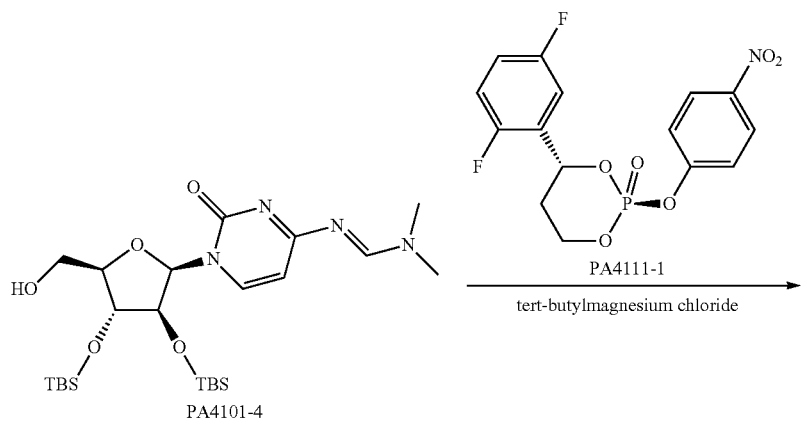

-continued

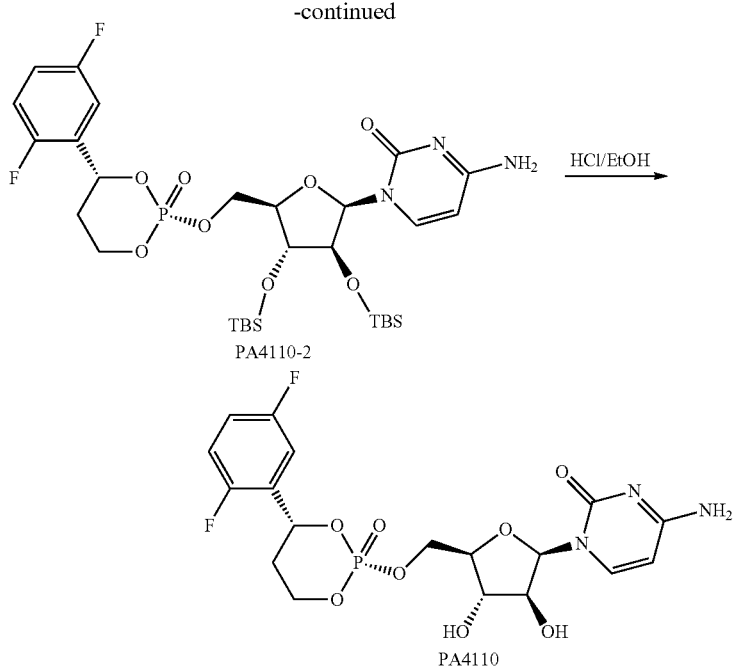

PA4110-2

PA4110

Experimental Section:

Step 1) Synthesis of Compound PA4110-2:

dissolving a compound PA4101-4 (330 mg, 0.6 mmol) in tetrahydrofuran (10 mL) under nitrogen protection, cooling the mixture in ice bath to 0° C., slowly adding 1 M tert-butylmagnesium chloride solution (3 mL, 3 mmol) dropwise, after completing the dropwise addition, stirring the reaction solution at room temperature for 1 hour, and cooling the reaction solution again to 0° C., adding PA4110-1 (0.3 g, 0.8 mmol), stirring the mixture at room temperature overnight, after completing the reaction, quenching the reaction with saturated ammonium chloride solution (30 mL), followed by extraction with ethyl acetate (3×150 mL), washing with saturated brine, drying over anhydrous sodium sulfate, spin-drying, and separating and purifying by silica gel chromatographic column to obtain a white solid compound PA4110-2 (200 mg), with yield of 45%.

Step 2) Synthesis of Target Compound PA4110:

dissolving the compound PA4110-2 (200 mg, 0.28 mmol) in 3.6% hydrochloric alcohol solution (3 ml), and carrying out reaction while stirring at room temperature overnight, after TLC showed completion of reaction, adjusting a pH value to 8-9 with aqueous ammonia, after removing ethanol by rotary evaporation, adding water (50 mL), followed by extraction with ethyl acetate (3×50 mL), washing an organic phase with saturated brine, drying over anhydrous sodium sulfate, followed by filtration, spin-drying, and purification by Combiflash chromatography column to obtain a white solid PA4110 (70 mg), with yield of 52%.

Example 11 PA4111

Synthesis Route:

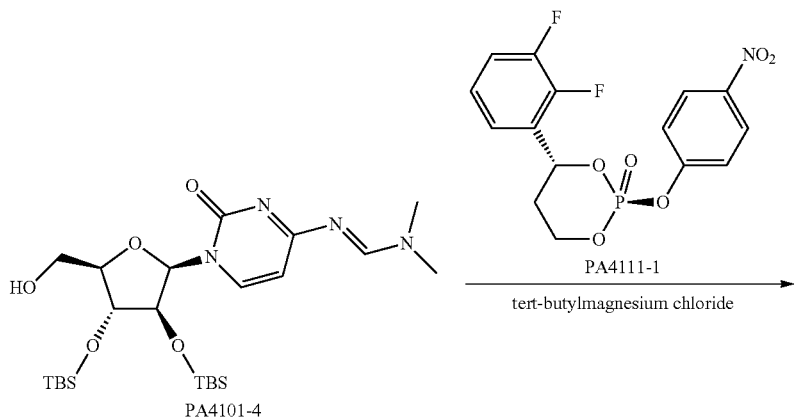

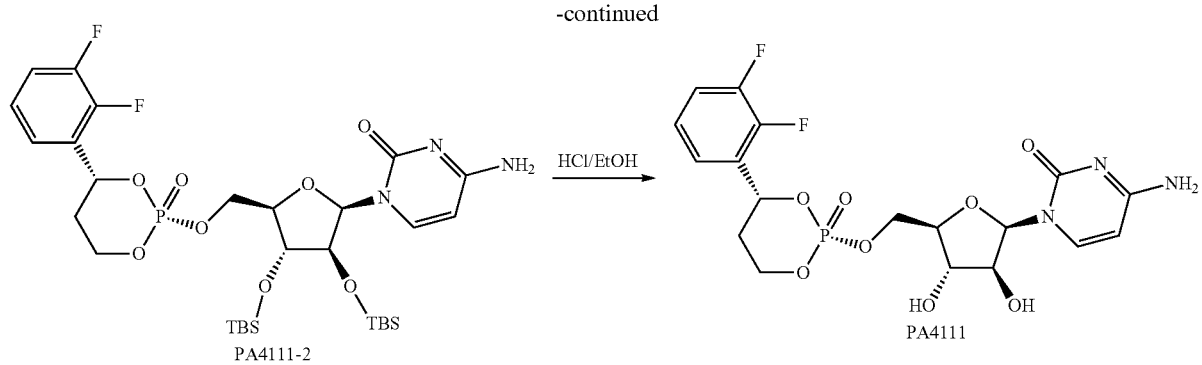

Experimental Section:

Step 1) Synthesis of Compound PA4111-2 dissolving a compound PA4101-4 (200 mg, 0.38 mmol) in tetrahydrofuran (10 mL) under nitrogen protection, cooling the mixture in ice bath to 0° C., slowly adding 1 M tert-butylmagnesium chloride solution (1.4 mL, 1.4 mmol) dropwise, after completing the dropwise addition, stirring the reaction solution at room temperature for 1 hour, and cooling the reaction solution again to 0° C., adding PA4111-1 (211 mg, 0.57 mmol), stirring the mixture at room temperature overnight, after completing the reaction, quenching the reaction with saturated ammonium chloride solution (30 mL), followed by extraction with ethyl acetate (3×150 mL), washing with saturated brine, drying over anhydrous sodium sulfate, spin-drying, and separating and purifying by silica gel chromatographic column to obtain a white solid compound PA4111-2 (100 mg), with yield of 34%.

Step 2) Synthesis of Target Compound PA4111:

dissolving the compound PA4111-2 (230 mg, 0.31 mmol) in 3.6% hydrochloric alcohol solution (15 ml), and carrying out reaction while stirring at room temperature overnight, after TLC showed completion of reaction, adjusting a pH value to 8-9 with aqueous ammonia, after removing ethanol by rotary evaporation, adding water (50 mL), followed by extraction with ethyl acetate (3×50 mL), washing an organic phase with saturated brine, drying over anhydrous sodium sulfate, followed by filtration, spin-drying, and purification by Combiflash chromatography column to obtain a white solid PA4111 (30 mg), with yield of 48%.

TABLE 1

Compounds prepared in the above examples

| Compound No. | Structure | Molecular Weight |
|---|---|---|
| PA4101 | 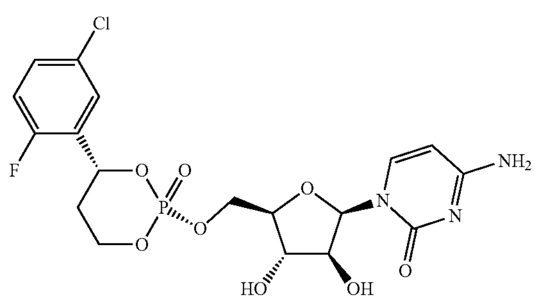 | 491.79 |
| PA4102 | 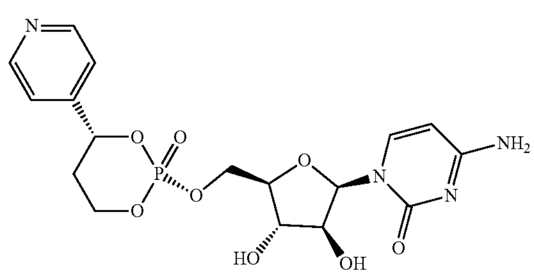 | 440.34 |

TABLE 1-continued

Compounds prepared in the above examples

| Compound No. | Structure | Molecular Weight |
|---|---|---|
| PA4103 | (3,5-dichlorophenyl cyclic phosphate ester of cytidine) | 508.24 |
| PA4104 | (3,5-difluorophenyl cyclic phosphate ester of cytidine) | 475.34 |
| PA4105 | (3-chloro-4-fluorophenyl cyclic phosphate ester of cytidine) | 491.79 |
| PA4106 | (4-chloro-3-fluorophenyl cyclic phosphate ester of cytidine) | 491.79 |
| PA4107 | (3-chloro-2-fluorophenyl cyclic phosphate ester of cytidine) | 491.79 |

TABLE 1-continued

Compounds prepared in the above examples

| Compound No. | Structure | Molecular Weight |
|---|---|---|
| PA4108 | (structure: 2-chloro-5-fluorophenyl cyclic phosphate ester linked to cytidine) | 491.79 |
| PA4109 | (structure: 2,5-dichlorophenyl cyclic phosphate ester linked to cytidine) | 508.24 |
| PA4110 | (structure: 2,5-difluorophenyl cyclic phosphate ester linked to cytidine) | 475.34 |
| PA4111 | (structure: 2,3-difluorophenyl cyclic phosphate ester linked to cytidine) | 475.34 |

TABLE 2

Nuclear magnetism of the compounds prepared in each of the examples is shown in the following Table

| No. | Nuclear Magnetism Data |
|---|---|
| PA4101 | $^1$H NMR (400 MHz, DMSO-$d_6$) δ: 7.76 (d, J = 43.9 Hz, 2H), 7.68-7.57 (m, 2H), 7.52 (td, J = 8.6, 5.0 Hz, 1H), 7.40-7.20 (m, 1H), 6.11 (d, J = 3.6 Hz, 1H), 5.88 (d, J = 11.2 Hz, 1H), 5.80-5.51 (m, 3H), 4.68-4.38 (m, 2H), 4.27 (dt, J = 12.5, 6.8 Hz, 2H), 4.10-3.84 (m, 3H), 2.47-2.04 (m, 2H)ppm. |

TABLE 2-continued

Nuclear magnetism of the compounds prepared in each of the examples is shown in the following Table

| No. | Nuclear Magnetism Data |
|---|---|
| PA4102 Comparative Example | $^1$H NMR (400 MHz, DMSO-$d_6$) δ: 8.77-8.47 (m, 2H), 7.65-7.33 (m, 3H), 7.11 (d, J = 37.3 Hz, 2H), 6.11 (d, J = 3.7 Hz, 1H), 5.77 (d, J = 10.6 Hz, 1H), 5.70-5.48 (m, 3H), 4.52 (dd, J = 44.4, 8.6 Hz, 2H), 4.37-4.17 (m, 2H), 4.08-3.81 (m, 3H), 2.29-2.07 (m, 2H) ppm. |
| PA4103 | $^1$H NMR (400 MHz, DMSO-$d_6$) δ 7.63 (dd, J = 4.3, 2.5 Hz, 1H), 7.58-7.44 (m, 3H), 7.08 (d, J = 29.2 Hz, 2H), 6.12 (d, J = 3.7 Hz, 1H), 5.73 (d, J = 4.6 Hz, 1H), 5.68-5.53 (m, 3H), 4.61-4.38 (m, 2H), 4.29 (dd, J = 10.1, 6.0 Hz, 2H), 3.96 (dd, J = 7.2, 4.7 Hz, 2H), 3.90 (s, 1H), 2.22 (s, 2H)ppm |
| PA4104 | $^1$H NMR (400 MHz, CDCl$_3$) δ 7.53 (d, J = 7.4 Hz, 1H), 7.18 (d, J = 6.7 Hz, 3H), 7.13-6.93 (m, 2H), 6.11 (d, J = 3.5 Hz, 1H), 5.79-5.69 (m, 1H), 5.58 (d, J = 7.4 Hz, 1H), 4.62-4.36 (m, 2H), 4.28 (d, J = 7.2 Hz, 2H), 3.94 (d, J = 29.1 Hz, 3H), 2.21 (s, 2H)ppm. |
| PA4105 | $^1$H NMR (400, MHz, DMSO-$d_6$) δ 7.72-7.63 (m, 1H), 7.53 (d, J = 7.4 Hz, 1H), 7.46 (dd, J = 5.2, 3.3 Hz, 2H), 7.10 (d, J = 34.1 Hz, 2H), 6.12 (d, J = 3.7 Hz, 1H), 5.73 (d, J = 10.6 Hz, 1H), 5.60 (dd, J = 21.6, 6.0 Hz, 3H), 4.59-4.38 (m, 2H), 4.36-4.14 (m, 2H), 4.03-3.83 (m, 3H), 2.22 (dd, J = 17.6, 12.8 Hz, 2H)ppm |
| PA4106 | $^1$H NMR (400 MHz, DMSO-$d_6$) δ 7.63 (t, J = 8.0 Hz, 1H), 7.55-7.43 (m, 2H), 7.32 (d, J = 8.5 Hz, 1H), 7.06 (d, J = 34.8 Hz, 2H), 6.11 (d, J = 3.7 Hz, 1H), 5.80-5.69 (m, 1H), 5.60 (dd, J = 21.6, 7.4 Hz, 3H), 4.62-4.39 (m, 2H), 4.34-4.19 (m, 2H), 3.95 (ddd, J = 20.3, 12.6, 9.0 Hz, 3H), 2.28-2.09 (m, 2H)ppm. |
| PA4107 | $^1$H NMR (400 MHz, DMSO-$d_6$) δ 7.64 (d, J = 8.0 Hz, 1H), 7.59-7.49 (m, 2H), 7.30 (t, J = 8.0 Hz, 3H), 6.11 (d, J = 3.7 Hz, 1H), 5.93 (d, J = 11.1 Hz, 1H), 5.66 (d, J = 4.7 Hz, 2H), 5.59 (d, J = 7.6 Hz, 1H), 4.68-4.56 (m, 1H), 4.52-4.39 (m, 1H), 4.33-4.19 (m, 2H), 4.05-3.84 (m, 3H), 2.42-2.27 (m, 1H), 2.19 (s, 1H)ppm. |
| PA4108 | $^1$H NMR (400 MHz, DMSO) δ 7.59 (dd, J = 8.9, 5.1 Hz, 1H), 7.54 (d, J = 7.5 Hz, 1H), 7.43 (dd, J = 9.5, 3.0 Hz, 1H), 7.32 (td, J = 8.4, 3.1 Hz, 1H), 7.12 (d, J = 41.6 Hz, 2H), 6.12 (d, J = 3.6 Hz, 1H), 5.87 (d, J = 10.5 Hz, 1H), 5.63 (t, J = 4.0 Hz, 2H), 5.58 (d, J = 7.5 Hz, 1H), 4.69-4.58 (m, 1H), 4.53-4.40 (m, 1H), 4.38-4.26 (m, 2H), 3.98 (dd, J = 6.2, 3.9 Hz, 2H), 3.91 (s, 1H), 2.24 (dt, J = 24.9, 9.7 Hz, 2H)ppm |
| PA4109 | 1H NMR (400 MHz, DMSO) δ 7.59 (dt, J = 14.4, 4.0 Hz, 3H), 7.53-7.48 (m, 1H), 7.33 (d, J = 86.0 Hz, 2H), 6.12 (d, J = 3.6 Hz, 1H), 5.92-5.82 (m, 1H), 5.64 (dd, J = 8.6, 4.1 Hz, 3H), 4.69-4.58 (m, 1H), 4.53-4.40 (m, 1H), 4.33 (t, J = 8.0 Hz, 2H), 4.00 (d, J = 5.0 Hz, 2H), 3.91 (s, 1H), 2.25 (dt, J = 27.1, 9.6 Hz, 2H)ppm |
| PA4110 | 1H NMR (400 MHz, DMSO) δ 7.54 (d, J = 7.4 Hz, 1H), 7.45-7.27 (m, 3H), 7.17 (d, J = 47.2 Hz, 2H), 6.11 (d, J = 3.5 Hz, 1H), 5.87 (d, J = 11.3 Hz, 1H), 5.61 (dd, J = 9.9, 6.1 Hz, 3H), 4.59 (d, J = 6.6 Hz, 1H), 4.47 (d, J = 13.7 Hz, 1H), 4.27 (dd, J = 13.7, 5.9 Hz, 2H), 3.97 (s, 2H), 3.89 (s, 1H), 2.43-2.30 (m, 1H), 2.15 (d, J = 14.7 Hz, 1H)ppm |
| PA4111 | $^1$H NMR (400 MHz, DMSO) δ 8.19-7.75 (m, 2H), 7.59-7.12 (m, 4H), 6.16-5.88 (m, 3H), 5.76 (s, 2H), 4.63 (s, 1H), 4.53-4.39 (m, 1H), 4.36-4.25 (m, 1H), 4.00 (dd, J = 25.9, 18.9 Hz, 4H), 2.39 (dd, J = 26.6, 12.3 Hz, 1H), 2.18 (d, J = 14.8 Hz, 1H)ppm |

Example 12 Evaluation of Recombinant Human CYP3A4 Metabolism In Vitro

Assay Method:

1) Source of Reagent

Recombinant human CYP3A4 enzyme was purchased from BD company, lot number 3100772.

Test compounds PA4101, PA4102, PA4103, PA4104, PA4105, PA4106, PA4107, PA4108, PA4109, PA4110 and PA4111 were synthesized by Zhejiang Palo Alto Pharmaceuticals, Inc., and dissolved in methanol (from Sinopharm Chemical Reagent Co., Ltd.) to prepare a storage solution of a concentration of 100 μM.

2) Reaction Process

Enzymatic reaction was carried out in 100 mM KH2PO4 buffer solution (pH 7.4), the concentration of the test compounds was 100 nM, the concentration of human liver microsomes was 0.1 nmol/ml, and NADPH concentration was 2 mM. The reaction was initiated by NADPH finally added, and after reaction for 1, 5, 10, 20, 30 min in a constant-temperature shaking water bath kettle, samples were taken, and 1.5 times of volume of methanol was immediately added to terminate the reaction.

3) Sample Processing and Analysis Method

I Sample Pretreatment:

The centrifugation was carried out for 20 minutes at a maximum speed of 13,600 rpm using an Eppendorf tabletop centrifuge. Supernatant was taken, and after being blow-dried by a nitrogen blower, the supernatant was re-dissolved into a mobile phase A (0.1% formic acid v/v aqueous solution).

| II Liquid Phase Gradient: | | |
|---|---|---|
| Time (minute) | Mobile Phase A (0.1% FA in $H_2O$) | Mobile Phase B (acetonitrile) |
| 0 | 99 | 1 |
| 1.1 | 30 | 70 |
| 1.5 | 5 | 95 |
| 2.2 | 99 | 1 |

Analytical column: Waters, Acquity UPLC HSS T3 column

Flow rate: 0.5 ml/min

Column temperature: 45° C.

III Mass Spectrometry Condition

An ion source was an electrospray ionization source (Turbo Ionspray); a positive ion mode; a capillary voltage was 3.0 kV; a temperature was 500° C.; a desolventizing airflow was 1000 L/h; and scan time, cone voltage, collision energy and ion response for quantitative analysis are shown in the following table (Table 3):

TABLE 3

Mass Spectrometry Conditions of Respective Analytes

| Analyte | Q1(m/z) | Q3(m/z) | Dwell (s) | Cone(V) | Collision(V) |
|---|---|---|---|---|---|
| PA4101 | 492 | 169 | 0.1 | 24 | 22 |
| PA4102 | 441 | 330 | 0.1 | 32 | 12 |
| PA4103 | 508 | 185 | 0.1 | 38 | 22 |
| PA4104 | 476 | 153 | 0.1 | 28 | 26 |
| PA4105 | 492 | 169 | 0.1 | 18 | 20 |
| PA4106 | 492 | 169 | 0.1 | 28 | 22 |
| PA4107 | 492 | 169 | 0.1 | 36 | 18 |
| PA4108 | 492 | 169 | 0.1 | 32 | 26 |
| PA4109 | 508 | 185 | 0.1 | 32 | 20 |
| PA4110 | 476 | 153 | 0.1 | 16 | 22 |
| PA4111 | 476 | 153 | 0.1 | 28 | 18 |

TABLE 4

Elimination Rate of Recombinant Human CYP3A4 Enzyme in vitro

| Compound | Elimination Rate in vitro ml/min/gprot |
|---|---|
| PA4101 | 35.0 |
| PA4102 | 3.26 |
| PA4103 | 23.1 |
| PA4104 | 2.93 |
| PA4105 | 5.79 |
| PA4106 | 14.9 |
| PA4107 | 8.28 |
| PA4108 | 23.6 |
| PA4109 | 67.3 |
| PA4110 | 8.37 |
| PA4111 | 9.55 |

The results show that all compounds were eliminated by recombinant human CYP3A4 enzyme in vitro, and different compounds had significant differences in the elimination rate. Unexpectedly, elimination rates of PA4109, PA4108 and PA4101 were much higher than that of PA4102 (currently clinical phase three). In the above, conversion rates of PA4109, PA4108 and PA4101 are about 20.6 times, 7.24 times and 10.7 times that of PA4102, respectively (Table 4). The higher the elimination rate was, the more active monophosphoric acid metabolites were generated, and the stronger pharmacological activity could be generated.

To sum up, as the compounds of the formula I and the formula II of the present disclosure have higher activity, the dosage required in treatment is lower, thus having higher safety and lower toxic and side effects.

All documents mentioned in the present disclosure are cited in the present disclosure as if each document was individually cited as reference. Beside, it should be understood that various changes or, modifications of the present disclosure could be made by those skilled in the art after reading the above teachings of the present disclosure, and these equivalents also fall, within the scope defined by the appended claims of the present disclosure.

What is claimed is:

1. A compound of formula (I), or an optical isomer, a pharmaceutically acceptable salt, a hydrate or a solvate thereof: wherein the compound is selected from the group consisting of:

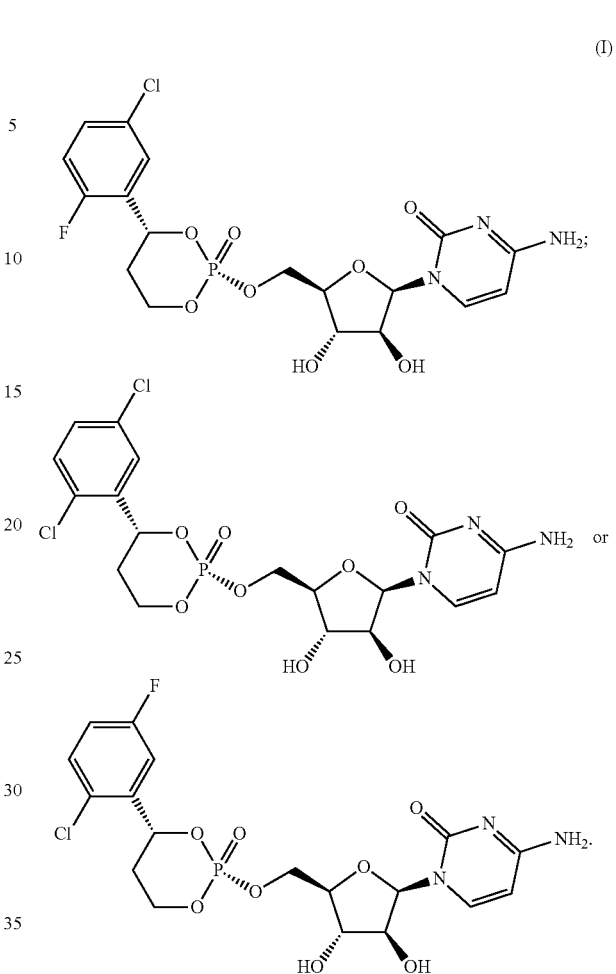

2. The compound according to claim 1, or an optical isomer, a pharmaceutically acceptable salt, a hydrate or a solvate thereof, characterized in that the pharmaceutically acceptable salt of the compound of formula (I) is a pharmaceutically acceptable salt formed from the compound of formula (I) with an inorganic acid or an organic acid, or formed from the compound of formula (I) with a base, wherein the compound of formula (I) or the salt thereof is amorphous or crystalline.

3. A pharmaceutical composition, comprising a therapeutically effective amount of the compound of claim 1, or an optical isomer, a pharmaceutically acceptable salt, a hydrate or a solvate thereof, and a pharmaceutically acceptable adjuvant, a diluent or a carrier.

4. A method for treating a liver cancer in a subject, comprising:
administering to the subject an effective amount of the compound, or an optical isomer, a pharmaceutically acceptable salt, a hydrate or a solvate thereof of claim 1.

* * * * *